US007625697B2

(12) United States Patent
Shalon et al.

(10) Patent No.: US 7,625,697 B2
(45) Date of Patent: *Dec. 1, 2009

(54) METHODS FOR CONSTRUCTING SUBARRAYS AND SUBARRAYS MADE THEREBY

(75) Inventors: Tidhar Dari Shalon, Atherton, CA (US); Patrick O. Brown, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 09/908,304

(22) Filed: Jul. 17, 2001

(65) Prior Publication Data

US 2001/0051344 A1 Dec. 13, 2001

Related U.S. Application Data

(63) Continuation of application No. 09/188,931, filed on Nov. 10, 1998, now abandoned, which is a continuation of application No. 08/514,875, filed on Aug. 14, 1995, now Pat. No. 7,378,236, which is a continuation-in-part of application No. 08/477,809, filed on Jun. 7, 1995, now Pat. No. 5,807,522, which is a continuation-in-part of application No. 08/261,388, filed on Jun. 17, 1994, now abandoned.

(51) Int. Cl.
*C12Q 1/68* (2006.01)
*C12M 1/36* (2006.01)
*C07H 21/04* (2006.01)

(52) U.S. Cl. .................... 435/6; 435/283.1; 435/287.2; 536/23.1

(58) Field of Classification Search ................ 435/6, 435/691; 702/19.2
See application file for complete search history.

(56) References Cited

U.S. PATENT DOCUMENTS

| 3,077,780 A | 2/1963 | Takatsy | 73/425.4 |
| 3,615,240 A | 10/1971 | Sanz | 23/259 |

(Continued)

FOREIGN PATENT DOCUMENTS

CA 1284931 6/1991

(Continued)

OTHER PUBLICATIONS

Gotteaman et al., Annual Review of Genetics, vol. 29, pp. 607-649, 1995.*

(Continued)

*Primary Examiner*—Michael Borin
(74) *Attorney, Agent, or Firm*—Howrey LLP

(57) ABSTRACT

A method and device for detecting or monitoring the treatment status of a selected physiological state or disease condition. The device has a subarray of genes which show a statistically significant change in gene level expression when compared with the control expression levels for that gene. The method involves applying a reporter-labeled messenger nucleic acid fraction to the array in the device, and comparing the pattern of gene expression on the array with that produced by labeled messenger nucleic acid from control cells. Also disclosed is a method of constructing the array.

10 Claims, 6 Drawing Sheets
(4 of 6 Drawing Sheet(s) Filed in Color)

U.S. PATENT DOCUMENTS

| | | | |
|---|---|---|---|
| 3,849,137 A | 11/1974 | Barzynski et al. | |
| 4,121,222 A | 10/1978 | Diebold et al. | 346/75 |
| 4,162,896 A | 7/1979 | Hosli | 23/230 R |
| 4,216,245 A | 8/1980 | Johnson | 427/2 |
| 4,269,933 A | 5/1981 | Pazos | |
| 4,325,913 A | 4/1982 | Wardlaw | 422/100 |
| 4,340,390 A | 7/1982 | Collins et al. | 23/230 B |
| 4,378,333 A | 3/1983 | Laipply | 422/100 |
| 4,395,486 A | 7/1983 | Wilson et al. | 435/6 |
| 4,516,833 A | 5/1985 | Fusek | |
| 4,517,338 A | 5/1985 | Urdea et al. | |
| 4,537,861 A | 8/1985 | Elings et al. | 436/518 |
| 4,586,546 A | 5/1986 | Mezei et al. | 141/2 |
| 4,588,682 A | 5/1986 | Groet et al. | 435/6 |
| 4,598,049 A | 7/1986 | Zelinka et al. | 435/287 |
| 4,631,211 A | 12/1986 | Houghten | 428/35 |
| 4,656,007 A | 4/1987 | Douchy et al. | 422/64 |
| 4,656,127 A | 4/1987 | Mundy | 435/6 |
| 4,668,476 A | 5/1987 | Bridgham et al. | 422/62 |
| 4,675,301 A | 6/1987 | Charneski et al. | 436/180 |
| 4,704,256 A | 11/1987 | Hood et al. | 422/68 |
| 4,713,326 A | 12/1987 | Dattagupta et al. | 435/6 |
| 4,715,413 A | 12/1987 | Backlund et al. | 141/94 |
| 4,728,502 A | 3/1988 | Hamill | |
| 4,737,344 A | 4/1988 | Koizumi et al. | 422/100 |
| 4,738,669 A | 4/1988 | Vlock | 604/289 |
| 4,746,490 A | 5/1988 | Saneii | 422/62 |
| 4,757,437 A | 7/1988 | Nishimura | 364/167 |
| 4,762,881 A | 8/1988 | Kauer | |
| 4,766,062 A | 8/1988 | Diamond et al. | 435/6 |
| 4,798,706 A | 1/1989 | Brigati | 422/102 |
| 4,811,062 A | 3/1989 | Tabata et al. | 356/152 |
| 4,811,218 A | 3/1989 | Hunkapiller et al. | 364/413.01 |
| 4,818,492 A | 4/1989 | Shimizu | 422/100 |
| 4,846,552 A | 7/1989 | Veldkamp et al. | |
| 4,861,866 A | 8/1989 | Durrum et al. | 530/333 |
| 4,877,745 A | 10/1989 | Hayes et al. | 436/166 |
| 4,886,741 A | 12/1989 | Schwartz | 435/5 |
| 4,888,278 A | 12/1989 | Singer et al. | 435/6 |
| 4,931,384 A | 6/1990 | Layton et al. | 435/7 |
| 4,944,922 A | 7/1990 | Hayashi | 422/100 |
| 4,946,942 A | 8/1990 | Fuller et al. | |
| 4,965,188 A | 10/1990 | Mullis et al. | 435/6 |
| 4,973,493 A | 11/1990 | Guire | 427/2 |
| 4,981,783 A | 1/1991 | Augenlicht | |
| 4,981,985 A | 1/1991 | Kaplan et al. | |
| 4,984,100 A | 1/1991 | Takayama et al. | |
| 5,006,464 A | 4/1991 | Chu et al. | 435/7.1 |
| 5,011,770 A | 4/1991 | Kung et al. | 435/6 |
| 5,026,773 A | 6/1991 | Steel | 525/54.11 |
| 5,028,525 A | 7/1991 | Gray et al. | 435/6 |
| 5,037,882 A | 8/1991 | Steel | 525/54.11 |
| 5,059,398 A | 10/1991 | Kenney | 422/100 |
| 5,063,081 A | 11/1991 | Cozzette et al. | 427/2 |
| 5,077,085 A | 12/1991 | Schnur et al. | 427/98 |
| 5,077,210 A | 12/1991 | Eigler et al. | 435/176 |
| 5,079,600 A | 1/1992 | Schnur et al. | 357/4 |
| 5,094,594 A | 3/1992 | Brennan | 417/322 |
| 5,096,807 A | 3/1992 | Leaback | 435/6 |
| 5,100,626 A | 3/1992 | Levin | 422/100 |
| 5,143,849 A | 9/1992 | Barry et al. | 436/50 |
| 5,143,854 A * | 9/1992 | Pirrung et al. | 436/518 |
| 5,164,319 A | 11/1992 | Hafeman et al. | 435/291 |
| 5,171,695 A | 12/1992 | Ekins | 436/501 |
| 5,175,209 A | 12/1992 | Beattie et al. | 525/54.11 |
| 5,258,506 A | 11/1993 | Urdea et al. | |
| 5,324,633 A | 6/1994 | Fodor et al. | 435/6 |
| 5,424,188 A | 6/1995 | Schneider et al. | 435/6 |
| 5,432,099 A | 7/1995 | Ekins | 436/518 |
| 5,436,327 A | 7/1995 | Southern et al. | 536/25.34 |
| 5,445,934 A * | 8/1995 | Fodor et al. | 435/6 |
| 5,445,940 A * | 8/1995 | Brenner et al. | 435/7.24 |
| 5,451,683 A | 9/1995 | Barrett et al. | |
| 5,455,008 A | 10/1995 | Earley et al. | 422/100 |
| 5,465,629 A | 11/1995 | Waylett, Jr. | 73/864.24 |
| 5,492,806 A | 2/1996 | Drmanac et al. | 435/5 |
| 5,525,464 A | 6/1996 | Drmanac et al. | 435/6 |
| 5,532,128 A | 7/1996 | Eggers et al. | 435/16 |
| 5,569,584 A | 10/1996 | Augenlicht | 435/6 |
| 5,599,720 A | 2/1997 | Ekins | 436/501 |
| 5,604,099 A | 2/1997 | Erlich et al. | 435/6 |
| 5,627,025 A * | 5/1997 | Steinman et al. | 435/5 |
| 5,695,940 A | 12/1997 | Drmanac et al. | 435/6 |
| 5,763,262 A | 6/1998 | Wong et al. | 435/287.2 |
| 5,795,716 A | 8/1998 | Chee | |
| 5,800,992 A * | 9/1998 | Fodor et al. | 435/6 |
| 5,830,645 A * | 11/1998 | Pinkel et al. | 435/6 |
| 6,013,449 A | 1/2000 | Hacia et al. | |
| 6,040,166 A | 3/2000 | Erlich et al. | 435/194 |
| 6,045,996 A | 4/2000 | Cronin et al. | |
| 6,171,843 B1 | 1/2001 | Bandman et al. | |
| 7,442,499 B2 * | 10/2008 | Brown et al. | 435/6 |

FOREIGN PATENT DOCUMENTS

| | | |
|---|---|---|
| EP | 0046083 A2 | 2/1982 |
| EP | 0103197 A1 | 3/1984 |
| EP | 0 130 523 A2 | 1/1985 |
| EP | 0130739 A2 | 1/1985 |
| EP | 0 142 299 A2 | 5/1985 |
| EP | 0142299 A2 | 5/1985 |
| EP | 0 171 150 A2 | 2/1986 |
| EP | 0 185 547 A2 | 6/1986 |
| EP | 0 194 132 A2 | 9/1986 |
| EP | 0194132 A2 | 9/1986 |
| EP | 0 228 075 A2 | 7/1987 |
| EP | 0228075 A2 | 7/1987 |
| EP | 0 237 362 A1 | 9/1987 |
| EP | 0237362 A1 | 9/1987 |
| EP | 0238332 A2 | 9/1987 |
| EP | 0 260 965 A2 | 3/1988 |
| EP | 0268237 A2 | 5/1988 |
| EP | 0 304 202 B1 | 2/1989 |
| EP | 0 328 256 A1 | 8/1989 |
| EP | 0328256 A1 | 8/1989 |
| EP | 0 373 203 A | 6/1990 |
| EP | 0 392 546 A2 | 10/1990 |
| EP | 0392546 A2 | 10/1990 |
| GB | 2156074 A | 10/1985 |
| GB | 2196476 A | 4/1988 |
| JP | 62-254034 | 11/1987 |
| WO | WO 85/01051 | 3/1985 |
| WO | WO 86/00991 | 2/1986 |
| WO | WO 86/06487 | 11/1986 |
| WO | WO 86/06487 A1 | 11/1986 |
| WO | WO 88/01058 A1 | 2/1988 |
| WO | WO 88/01302 A1 | 2/1988 |
| WO | WO 90/00626 A1 | 1/1990 |
| WO | WO 90/02605 A1 | 3/1990 |
| WO | WO 90/04652 | 5/1990 |
| WO | WO 90/07582 A1 | 7/1990 |
| WO | WO 91/00868 A1 | 1/1991 |
| WO | WO 91/07087 A1 | 5/1991 |
| WO | WO 92/10092 A1 | 6/1992 |
| WO | WO 93/09668 | 6/1992 |
| WO | WO 92/10588 | 5/1993 |
| WO | WO 93/17126 A1 | 9/1993 |

OTHER PUBLICATIONS

Freeman et al., Cancer Research, vol. 49, pp. 6221-6225 (1989).*
Gomella et al., Cancer Research, vol. 49, pp. 6972-6975 (1989).*
Pease et al. Proc. Natl. Acad. Sci , 91, 5022-5026, 1994.*

Monaco, Lehrach et al., Abstract of paper presented at 1989 Meeting on Genome Sequencing and Mapping (Cold Spring Harbor Press) p. 90, Human Genome Linking with Cosmids and Yeast Artificial Chromosomes, Apr. 26, 1989.

Hoheisel, Lehrach et al., Adv. Mol. Gen. 4:125-132, Use of high coverage libraries for an integrated analysis of genomic DNA, 1991.

Meinkoth & Wahl, Anal, Biochem. 138:267-284, Hybridization of Nucleic Acids Immobilized on Solid Supports, 1984.

Dattagupta et al., Anal. Biochem. 177:85-89, Rapid Identification of Microorganisms by Nucleic Acid Hybridization after Labeling the Test Sample, 1989.

Kerkof & Kelly, Anal. Biochem. 188:349-355, A Procedure for Making Simultaneous Determinations of the Relative Levels of Gene Transcripts in Tissues or Cells, 1990.

Newman & Turner, Analytica ChImica Acta 262:13-17 (1992), Ink-jet printing for the fabrication of amperometric glucose biosensors, 1992.

Teng & Vest, Appl. Math. Modelling 12:182-188 (1988), Mathematical models of ink jet printing in thick-film hybrid microelectronics, Apr. 1988.

Kuriyama, Applied Biosensors (Donald Wise Ed.) Butterworths pp. 93-114 (1989), An ISFET Biosensor, 1989.

Frumgarts et al., Bioorg Khim, 12:1508-13 (1986), Preparation of fluorescent-labeled DNA and its use as a probe in molecular hybridization, 1986.

Uber et al., BioTechniques 11(5):642-647, Application of robotics and image processing to automated colony picking and arraying., Nov. 1991.

Ekins and Chu, Clin. Chem. 37(11):1955-1967, Multianalyte Microspot Immunoassay-Microanalytical 'Compact Disk' of the Future, 1991.

Bannwarth et al., DNA 5(5):413-419 (1986), Laboratory Methods: A System for the Simultaneous Chemical Synthesis of Different DNA Fragments on Solid Support, 1986.

Arnold et al., Federation Proceedings 43(7) Abstract No. 3669 (1984), A Novel Universal Support of DNA & RNA Synthesis, 1984.

Takada et al., Fujitsu Sci. Tech. J. 22(2):132-138, Effect of Ink Channel Dimensions and Fluid Viscosity in Drop-on-Demand Ink-Jet Printing, Jun. 1986.

Hanahan & Meselson, Gene 10:63-67, Plasmid Screening at High Colony Density, 1980.

Lewin, Genes, John Wiley & Sons, New York, 1987.

Zischler, Epplen et al., Hum. Gen. 82:227-233, Digoxigenated oligonucleotide probes specific for simple repeats in DNA fingerprinting and hybridization in situ, 1989.

Teng & Vest, IEEE Trans. Indus. Elec. 35(3):407-412, A Microprocessor-Controlled Ink Jet Printing System for Electronic Circuits, Aug. 1988.

Bhatia et al., J. Am. Chem. Soc. 114:4432-4433, New Approach To Producing Patterned Biomolecular Assemblies, Feb. 1, 1992.

Kyser et al., J. Appl. Photographic Eng. 7(3):73-79 (1981), Design of an Impulse Ink Jet, Jun. 1981.

Wallace, J. Electronic Packaging 36(5):108-111, Automated Electronic Circuit Manufacturing Using Ink-Jet Technology, Jun. 1989.

Raoult and Dasch, J. Immunological Meth. 125:57-65, The Line Blot: an immunoassay for monoclonal and other antibodies, 1989.

Hoheisel, Lehrach et al., J. Mol. Biol. 220:903-914 (1991), Use of High Coverage Reference Libraries of Drosophila melanogaster for Relational Data Analysis, Aug. 20, 1991.

Southern, J. Mol. Biol. 98:503-517 (1975), Detection of Specific Sequences Among DNA Fragments Separated by Gel Electrophoresis, Nov. 5, 1975.

Bernardini et al., J. Neuroscience Meth. 38:81-88, Applications of Piezoelectric Fluid Jetting Devices to Neuroscience Research, 1991.

Ekins, J. Pharm. Biomed. Anal. 7(2):155-168, Multi-analyte immunoassay, 1989.

Bains and Smith, J. Theor. Biol. 135:303-307 (1988), A Novel Method for Nucleic Acid Sequence Determination, 1988.

Longmire et al., LRA 3:195-198 (1991), Automated Construction of High-Density Gridded Arrays of Chromosome-Specific Cosmid Libraries, 1991.

Beltz et al., Meth. Enzymology 100(19):266-285, Isolation of Multigene Families and Determination of Homologies by Filter Hybridization Methods, 1983.

Hanahan & Meselson, Meth. Enzymology 100:333-342, Plasmid Screening at High Colony Density, 1983.

Miyada et al., Meth. Enzymology 154:94-107, Oligonucleotide Hybridization Techniques, 1987.

Kidd et al., Nature 304:230-234, alpha-1Antitrypsin deficiency detection by direct analysis of the mutation of the gene, Jul. 21, 1983.

Saiki et al., Nature 324:163-166, Analysis of Enzymatically Amplified B-Globin and HLA-DQa DNA With Allele-Specific Oligonucleotide Probes, Nov. 13, 1986.

Lichter and Ward, Nature 345:93-94, Is non-isotopic in situ hybridization finally coming of age?, May 3, 1990.

Little, Nature 346:611-612, Clone maps made simple, Aug. 16, 1990.

Ohtsuka et al., Nuc. Acids Res. 1(10):1351-1357, Studies on transfer ribonucleic acids and related compounds, Oct. 1974.

Seed, Nuc. Acids Res. 10(5):1799-1810, Diazotizable arylamine cellulose papers for the coupling and hybridization of nucleic acids, 1982.

Frank et al., Nuc. Acids Res. 11(13):4365-4377 (1983), A new general approach for the simultaneous chemical synthesis of large numbers of oligonucleotides: segmental solid supports, Jun. 8, 1983.

Renz & Kurz, Nuc. Acids Res. 12: 3435-3144, A colorimetric method for DNA hybridization, 1984.

Ghosh & Musso, Nuc. Acids Res. 15(13):5353-5372, Covalent attachment of oligonucleotides to solid supports, 1987.

Gingeras et al., Nuc. Acids Res. 15(13):5373-5390 (1987), Hybridization Properties of Immobilized Nucleic Acids, 1987.

Hodgson and Fisk, Nuc. Acids Res. 15(15):6295, Hybridization probe size control: optimized 'oligolabeling', 1987.

Schafer, Epplen et al., Nuc. Acids Res. 16(19):9344, DNA fingerprinting using non-radioactive oligonucleotide probes specific for simple repeats, 1988.

Zischler, Epplen et al., Nuc. Acids Res. 17(11):4411, Non-radioactive oligonudeotide fingerprinting in the gel, 1989.

Anand et al., Nuc. Acids Res. 18(8):1951-1956, A 3.5 genome equivalent multi access YAC library:construction, characterization, screening and storage., 1990.

Nizetic, Lehrach et al., Nuc. Acids Res. 19(1):182, An improved bacterial colony lysis procedure enables direct DNA hybridization using short (10,11 bases) oligonucleotides to cosmids., Jan. 11, 1991.

Baxendale, Lehrach et al., Nuc. Acids Res. 19(23):6651, The direct screening of cosmid libraries with YAC clones, Dec. 11, 1991.

Maskos and Southern, Nuc. Acids Res. 20(7):1679-1684, Oligonucleotide hybridisations on glass supports, Mar. 9, 1992.

Kafatos et al., Nuc. Acids Res. 7(6):1541-1552, Determination of nucleic acid sequence homologies and relative concentrations by a dot hybridization procedure, Nov. 24, 1979.

Wallace et al., Nuc. Acids Res. 9(4):879-894, The use of synthetic Oligonucleotides as Hybridization Probes II: Hybridization of oligonucleotides of mixed sequence to rabbit b-globin DNA; 1981.

Anderson & Young, Nucleic Acid Hybridisation: a practical approach, ed. Hames, B.D., & Higgins, S.J., (IRL Press, Oxford) Chapter 4, Quantitative Filter Hybridisation.

Dattagupta et al., Perspectives in Antiinfective Therapy (Jackson et al., Eds. 1988) pp. 241-247, Nucleic Add Hybridization: A Rapid Method for the Diagnosis of Infectious Diseases, Sep. 3, 1988.

Teng, Kien Fei Robert, Ph.D. Thesis 35372 Purdue University, Ink Jet Printing in Thick Film Hybrid Microelectronics, Dec. 19, 1986.

Ellis, Pharmaceutical Res. 3(4):195-207 (1986), The Applications of Synthetic Oligonucleotides to Molecular Biology., 1986.

Lasky et al., Proc. Nat'l. Acad. Sci. USA 77(9):5317-5321, Messenger RNA prevalence in sea urchin embryos measured with cloned cDNAs, Sep. 1986.

Wood et al., Proc. Nat'l. Acad. Sci. USA 82:1585-1588, Base composition-independent hybridization in tetramethlammonium chloride: a method for oligonucleotide screening of highly complex gene libraries, Mar. 1985.

Olson et al., Proc. Nat'l. Acad. Sci. USA 83:7826-7830, Random-clone strategy for genomic restriction mapping in yeast, Oct. 1986.

Strezoska, Drmanac, et al., Proc. Nat'l. Acad. Sci. USA 88:10089-10093, DNA sequencing by hybridization: 100 bases read by a non-gel-based method, Nov. 1991.

Nizetic, Lehrach et al., Proc. Nat'l. Acad. Sci. USA 88:3233-3237, Construction, Arraying and High Density Screening of Large Insert Libraries of Human Chromosomes X and 21, Apr. 1991.

Larin, Lehrach, et al., Proc. Nat'l. Acad. Sci. USA 88:4123-4127, Yeast artificial chromosome libraries containing large inserts from mouse and human DNA, May 1991.

Wallace et al., Proceedings, Bioprocess Eng. Symp. 1989 (Diller et al., eds.), Application of Ink-Jet Technology to Neuroscience Research and Biomedical Research, Dec. 1989.

Hayes & Wallace, Proceedings, ISHM '89, Application of Ink-Jet Technology to Microelectronic Packaging, Oct. 1989.

Abbott et al., Science 257:1380-1382, Manipulation of the Wettability of Surfaces on the 0.1-to 1-Micrometer Scale Through Micromachining and Molecular Self-Assembly, 1992.

Tonucci et al., Science 258:783-785, Nanochannel Array Glass, Oct. 30, 1992.

Bhatia et al., Sensors and Actuators B3:311-317, Immobilization of Acetylcholinesterase on Solid Surfaces: Chemistry and Activity Studies, 1991.

Ross et al., Techniques For The Analysis Of Complex Genomes Ch. 8 pp. 137-153, High-Density Gridded YAC Filters: their Potential as Genome Mapping Tools, 1992.

Frank et al., Tetrahedron 44:6031-6040, Simultaneous Multiple Peptide Synthesis Under Continuous Flow Conditions on Cellulose Paper Discs as Segmental Solid Supports, 1988.

Matthes et al., The EMBO Journal 3(4):801-805 (1984), Simultaneous Rapid Chemical Synthesis of Over One Hundred Oligonucleotides on a Microscale, 1984.

Southern et al., "*Molecular Interactions on Microarrays*," Nature Genetics Supplement 21: 5-9 (1999).

Lipshute et al., "*Using Oligonucleotide Probe Arrays to Access Genetic Diversity*," BioTechniques 19(3): 442-447 (1995).

Lockhart et al., "*Expression Monitoring by Hybridization to High-Density Oligonucleotide Arrays*," Nature Biotehchnology 14: 1675-1680 (1996).

Schechtman, "*Isolation of Telomere DNA from Neurospora crassa*," Molecular and Cellular Biology 7(9): 3168-3177 (1987).

Rosenbluth et al., "*Pairing for Recombination in LGV of Caenorhabditis elegans: A Model Based on Recombination in Deficiency Heterozygotes*," Genetics 124: 615-625 (1990).

Clark et al., "*Analysis of Lethal Mutations Induced in a Mutator Strain that Activates Transposable Elements in Caenorhabditis elegans*," Genome 33: 109-114 (1990).

Pritchard et al,, "*Nucleotide Sequence of the Mitochondrial Genome of Paramecium*," Nucleic Acids Research 18(1): 173-180(1990).

Adams et al., "*Complementary DNA Sequencing: Expressed Sequence Tags and Human Genome Project*," Science 252: 1651-1656(1991).

Hedgecock et al., "*The unc-5, unc-6, and unc-40 Genes Guide Circumferential Migrations of Pioneer Axons and Mesodermal Cells on the Epidermis in C. elegans*," Neuron 2: 61-85 (1990).

Broach, "*Genes of Saccharomyces cerevisiae*," The Molecular Biology of the Yeast Saacharomyces, Cold Spring Harbor Laboratory, pp. 653-657 (1981).

Sundberg et al., "Spatially-Addressable Immobilization of Macromolecules on Solid Supports," J. Am. Chem. Soc. 117(49): 12050-12057 (1995).

Amy Savage Blawas, "*Photopatterning of Protein Features Using Caged-Biotin-Bovine Serum Albumin*," Ph.D. Dissertation, Department of Biomedical Engineering, Duke University (1998).

Forman et al., "*Thermodynamics of Duplex Formation and Mismatch Discrimination on Photolithographically Synthesized Oligonucleotide Arrays*," ACS Symposium Series, Molecular Modeling of Nucleic Acids 682: 206-228 (1998).

Maskes et al., "*Oligonucleotide Hybridisations on Glass Supports: a Novel Linker for Oligonucleotide Synthesis and Hybridisation Properties of Oligonucleotides Synthesized in situ*," Nucleic Acids Research 20(7): 1679-1684 (1992).

Marshall et al., "*DNA Chips: an Array of Possibilities*," Nature Biotechnology 16: 27-31 (1998).

Blawas et al., "*Step-and-Repeat Photopatterning of Protein Features Using Caged-Biotin-BSA: Characterization and Resolution*," Langmuir 14: 4243-4250 (1998).

Bannwarth et al., "*Laboratory Methods, A system for the Simultaneous Chemical Synthesis of Different DNA fragments on Solid Support*," DNA 5(5): 413-419 (1986).

Geysen et al., "*Strategies for Epitope Analysis Using Peptide Synthesis*," J. Immunological Methods 102: 259-274 (1987).

Chu et al.,"*Microarray-Based Immunoassays*," Immunochemical Technology for Environmental Applications, American Cancer Society, pp. 170-184 (1997).

Meier-Ewert et al., "*An Automated Approach to Generating Expressed Sequence Catalogues*," Nature 361: 375-376 (1993).

Nizetic et al., "*Construction, Arraying, and High-Density Screening of Large Insert Libraries of Human Chromosomes X and 21: Their Potential Use as Reference Libraries*," Proc. Natl. Acad. Sci. USA 88: 3233-3237 (1991).

Raoult et al., "*The line Blot: an Immunoassay for Monoclonal and Other Antibodies, Its Application to the Serotyping of Gram-Negative Bacteria*," J. Immunological Methods 125: 57-65 (1989).

Gray et al., "*Exploiting Chemical Libraries, Structure, and Genomics in the Search for Kinase Inhibitors*," Science 281: 533-538 (1998).

Cronin et al., "*Cystic Fibrosis Mutation Detection by Hybridization to Light-Generated DNA Probe Arrays*," Human Mutation 7: 244-255 (1996).

Saizieu et al., "*Bacterial Transcript Imaging by Hybridization of Total RNA to Oligonucleotide Arrays*," Nature Biotechnology 16: 45-48 (1998).

Hacia et al., "*Detection of Heterozygous Mutations in BRCA1 Using High Density Oligonucleotide Arrays and Two-Color Fluorescence Analysis*," Nature Genetics 14: 441-447 (1996).

Wang et al., "*Large-Scale Identification, Mapping, and Genotyping of Single-Nucleotide Polymorphisms in the Human Genome*," Science 280: 1077-1082 (1998).

Greenberg et al., "*Cleavage of Oligonucleotides from Solid-Phase Supports Using o-Nitrobenzyl Photochemistry*," J. Org. Chem. 59: 746-753 (1994).

Yoo et al., "*Synthesis of Oligonucleotides Containing 3'-Alkyl Carboxylic Acids Using Universal, Photolabile Solid Phase Synthesis Supports*," J. Org. Chem. 60: 3358-3364 (1995).

Zammattao et al., "*Comparison between Different Strategies of Covalent Attachment of DNA to Glass Surfaces to Build DNA Microarrays*," Analytical Biochemistry 280: 143-150 (2000).

\* cited by examiner

METHODS FOR CONSTRUCTING SUBARRAYS AND SUBARRAYS MADE THEREBY

This invention is a continuation of U.S. Ser. No. 09/188,931, filed Nov. 10, 1998 now abandoned, which is a continuation of U.S. Ser. No. 08/514,875, filed Aug. 14, 1995 now U.S. Pat. No. 7,378,236, which is a continuation-in part of U.S. Ser. No. 08/477,809, filed Jun. 7, 1995 now U.S. Pat. 5,807,522, which is a continuation-in-part of U.S. Ser. No. 08/261,388, filed Jun. 17, 1994 now abandoned, all of which are incorporated herein by reference.

The United States government may have certain rights in the present invention pursuant to Grant No. HG00450 by the National Institutes of Health.

FIELD OF THE INVENTION

This invention relates to a method and gene-array device for detecting and monitoring gene expression levels specifically related to a given disease-related state, and to a method for constructing the gene-array device.

REFERENCES

Ausubel, F. M., et al., CURRENT PROTOCOLS IN MOLECULAR BIOLOGY (John Wiley and Sons, Inc., Media, Pa.).

Cole, C. G., et al., Genomics 14:931-8 (1992).

Diamandis E. P., Critical Rev in Clinical Laboratory Sci, 1992, 29(3-4):269-305.

Lehrach, et al., HYBRIDIZATION FINGERPRINTING IN GENOME MAPPING AND SEQUENCING, GENOME ANALYSIS. VOL 1 (Davies and Tilgham, Eds.), Cold Spring Harbor Press, pp. 39-81 (1990).

Lytras A., et al., Endocrinology, 1994 June, 134(6):2461-7.

Maniatis, et al., MOLECULAR CLONING, A LABORATORY MANUAL, Cold Spring Harbor Press (1989).

Manoni, M., et al., Biotechniques 12:48-50, 52-3 (1992).

Maser R. L., et al., Seminars in Nephrology, 1995 January, 15(1):29-42.

Mullis, K. B., U.S. Pat. No. 4,683,202, issued 28 Jul. 1987a.

Mullis, K. B., et al., U.S. Pat. No. 4,683,195, issued 28 Jul. 1987b.

Nelson, et al., Nature Genetics 4:11-18 (1993).

Orr S. L., et al., Proc Nat Acad Sci, USA, 1994 December 6, 91(25):11869-73.

Osterland C. K., Clinical Chemistry, 1994 November, 40(11 Pt 2):2146-53.

Piatak M. Jr, et al., Science, 1993 March 19, 259(5102):1749-54.

Sambrook J., et al., Molecular Cloning, A Laboratory Manual, Second Edition, Cold Spring Harbor Press, 1989.

Schena, M. et al., Proc. Nat. Acad. Sci. USA 89:3894-3898 (1992).

BACKGROUND OF THE INVENTION

A variety of methods for analyzing gene products and gene expression are available. Northern blot is one widely used method for monitoring gene expression (Sambrook et al). In this method, a cellular RNA fraction, typically total mRNA, is electrophoretically separated on a gel and the separated RNA species are transferred to a blot substrate. The RNA species are then hybridized with one or more labeled probes of interest, e.g., a labeled RNA or cDNA fragment on the substrate. The purpose of the method is to detect the size range and/or relative quantity of an expressed RNA species complementary to the labeled probe.

In general, sensitivity in the Northern blot is limited to mRNA species present at a level of about 1:10,000 of the total mRNA using radioactive detection, and Northern blots require up to 50 micrograms of mRNA per lane. Northern blots are labor intensive and in general not well suited to diagnostic applications.

The amplification step often required in Northern analysis may bias the relative abundance of discrete cDNA species in a complex mixture. Although methods which allow for reliable quantitation of the RT-PCR process (Piatak, et al) have been proposed, these are not practical for analysis of large numbers of genes.

It has also been proposed to analyze patterns of gene expression by hybridizing a gene of interest to colony blots of different cDNA libraries, where the frequency of hits provides a measure of "differential display" of the gene in the different tissues from which the cDNA libraries were originally made (Maser et al). This method requires the fabrication of a cDNA library and the labor-intensive analysis of unordered dot blots from the colony hybridizations.

Recently, there has been considerable interest in monitoring gene expression using tag sequencing. Here a cDNA library from a specific tissue type or disease state is made from poly A mRNA. Individual cDNA clones with inserts of 1-2 kb are selected at random and a "tag" of around 200 bases of each cDNA insert is sequenced. An expression profile is generated in the form of a computer database of the tag sequences for thousands of cDNA clones from the cDNA library (Orr). Computer analysis of expression profiles can determine which genes are differentially expressed in a specific tissue type or disease state. To date, however, the use of tag sequences has been limited by lack of information about the functional roles of most tag sequences, and in fact, assigning functional roles to tag sequences represents one of the challenging problems of the Human Genome Project.

In view of these limitations in identifying and quantitating gene expression levels for large numbers of expressed genes, it has not been practical heretofore to employ multi-gene expression as a sensitive test for cell status, e.g., in a disease state, or as a method for monitoring the effect of therapeutic treatment on diseased-state cells.

SUMMARY OF THE INVENTION

The invention includes, in one aspect, a method of constructing a subarray of genes whose gene expression levels are specifically related to the differences between test cells relative to control cells. The method includes first obtaining and preparing reporter-labeled copies of messenger nucleic acid from control cells in a population of control individuals, and from test cells in a population of test individuals having a shared phenotype of interest, e.g., a disease state, that is not present in control individuals.

The reporter-labeled nucleic acid from test and control cells is applied to a substrate having an array (e.g., a microarray) of at least $10^2$, and preferably $10^3$, distinct gene sequences. The nucleic acid is applied under conditions effective to hybridize the nucleic acid to complementary-sequence genes on the array.

The pattern of reporter levels for nucleic acids from the test cells is compared with that of nucleic acids from the control cells, and from this, the genes on the microarray which show a significant elevation or reduction in reporter levels, when compared with control levels, are identified. The array is formed with the identified genes.

The array is preferably a microarray formed on a single, contiguous substrate, at a density of at least $10^3$ distinct gene sequences per cm$^2$ surface area, and may contain $10^3$ to $10^4$ or more distinct gene sequences. Preferably, each distinct gene sequence is disposed at a separate, defined position in said array and is present in a defined amount between about 0.1 femtomole and 100 nanomoles.

The gene sequences forming the array may be obtained from a single tissue source or, preferably, from multiple tissue sources, and typically include cDNA sequences.

In one general embodiment, the test-cell nucleic acids from each test individual are applied to a separate array, and the genes of interest are identified by identifying those genes on the separate arrays which show a statistically significant elevation or reduction in reporter levels, when compared with control levels. In another general embodiment, the test-cell nucleic acids from the test individuals are pooled and applied to a single array.

The test- and control-cell nucleic acids may have different fluorescent reporters, allowing the nucleic acids from the test- and control cells to be applied to the same array. Alternatively, the test- and control-cell nucleic acids may be applied to different microarrays, with the same or different reporters.

In another aspect, the invention includes a method of detecting or monitoring the treatment status of a selected disease condition. In practicing the method, there is first prepared reporter-labeled copies of messenger nucleic acid obtained from test cells associated with the disease condition. The nucleic acid is applied to a subarray of genes which are characterized by a statistically significant increase or decrease in gene level expression, when compared with the level of gene expression in the same cell type or types in a control, non-disease state, under conditions effective to hybridize said nucleic acid species to complementary-sequence genes in said array. The levels of reporter associated with the genes in the array are determined, and from this, there is formed a pattern of gene expression. A comparison of the gene-expression pattern with a known pattern of gene expression associated with the disease condition, permits detection or monitoring of the treatment status of the disease state.

The method employs a gene-array device constructed according to another aspect of the invention. The device which includes a substrate, and a subarray of genes which each show a statistically significant increase or a statistically significant decrease in gene expression level when compared with the level of gene expression in a control cell type.

These and other objects and features of the invention will become more fully apparent when the following detailed description of the invention is read in conjunction with the accompanying figures.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

I. Definitions

Figure 1:
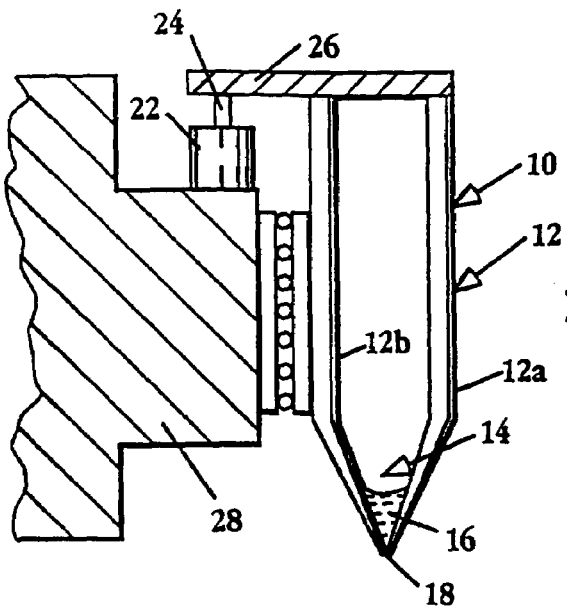
FIG. 1 is a side view of a solution-dispensing device having a open-capillary dispensing head constructed for use in one embodiment of the invention.

Unless indicated otherwise, the terms defined below have the following meanings:

"Distinct gene sequences" or "different gene sequences", as applied to the gene sequences forming an array or microarray or subarray, refers to polynucleotides containing distinct, i.e., different, gene sequences. The different-sequence polynucleotides may be partially or completely sequenced, as with expressed-sequence tags (EST's) or unsequenced, as with an unsequenced cDNA library.

An "array of distinct gene sequences" refers to a linear or two-dimensional array of distinct gene sequences, where the array may also contain regions with different graded concentrations of same-sequence polynucleotides, and/or mixtures of two or more distinct-sequence polynucleotides.

A "microarray of distinct gene sequences" refers to an array having a density of distinct gene sequences of at least about 100/cm$^2$, for example about 400/cm$^2$, and preferably at least about 1000/cm$^2$. The regions in a microarray have typical dimensions, e.g., diameters, in the range of between about 10-500 μm, for example about 250 μm, and are separated from other regions in the array by about the same distance, and contain typically, 0.1 femtomole to 100 nanomoles of nucleic acid molecules.

A "subarray of distinct gene sequences" is an array formed from a subset of gene sequences in a larger array. The subset is typically composed of gene sequences whose level of expression in cells in a selected physiological state or disease state obtained from a population of test individuals is significantly higher or lower than in control cells obtained from a population of control individuals.

"Cells of a given cell type or types" refers to cells obtained from one or more particular tissues or organs, e.g., hepatocytes, heart muscle cells, pancreatic cells, or non-differentiated embryonic tissue, or to a particular blood cell type or types, e.g., peripheral blood lymphocytes.

Cells having a "selected physiological state or disease condition" or "test cells" refer to cells of a given cell type or types which are (i) in a defined state of differentiation or activation, e.g., by gene activation, (ii) infected by a defined infectious agent, e.g., HIV-infected T cells, (iii) in a neoplastic state, i.e., tumor cells, (iv) in a chemical- or physical-response state, i.e., after exposure to a pharmacological agent with respect to control cells of the same type or types.

Cells of the same cell type or types as test cells, but which are (i) in a non-differentiated or non-activated state, (ii) uninfected, (iii) in a normal, non-neoplastic state, or (iv) in a control, no-drug state, are referred to herein as control cells.

A "population of test individuals" includes at least 5, and preferably 50 or more individuals all of whom share a common phenotype related to the individuals' test cells, e.g., individuals who all have a common disease or are infected by the same infectious agent.

A "population of control individuals" includes at least 5, and preferably 50 or more individuals all of whom share a common control phenotype related to the individuals' control cells, e.g., normal, disease-free and/or drug-free individuals, or share the same physiological state of other phenotype of interest.

"Reporter-labeled copies of messenger nucleic acid" refers to reporter-labeled mRNA transcripts obtained from test or control cells or cDNAs produced from such transcripts. The reporter label is any detectable reporter, and typically is a fluorescent reporter.

A support surface of an array is "hydrophobic" if a aqueous-medium droplet applied to the surface does not spread out substantially beyond the area size of the applied droplet. That is, the surface acts to prevent spreading of the droplet applied to the surface by hydrophobic interaction with the droplet.

A "meniscus" means a concave or convex surface that forms on the bottom of a liquid in a channel as a result of the surface tension of the liquid.

II. Method of Microarray Formation

This section describes a method of forming a microarray of distinct gene sequences on a solid support or substrate, for use in the method of the invention.

FIG. 1 illustrates, in a partially schematic view, a solution-dispensing device 10 useful in producing such a microarray. The device generally includes a dispenser 12 having an elongate open capillary channel 14 adapted to hold a quantity of the solution of a given-sequence gene or gene region, such as indicated at 16. The capillary channel is formed by a pair of spaced-apart, coextensive, elongate members 12a, 12b which are tapered toward one another and converge at a tip region 18 at the lower end of the channel.

With continued reference to FIG. 1, the dispenser device also includes structure for moving the dispenser rapidly toward and away from a support surface, for effecting deposition of a known amount of solution in the dispenser on a support, as will be described below with reference to FIGS. 2A-2C. In the embodiment shown, this structure includes a solenoid 22 which is activatable to draw a solenoid piston 24 rapidly downwardly, then release the piston, e.g., under spring bias, to a normal, raised position, as shown. The dispenser is carried on the piston by a connecting member 26, as shown.

The dispensing device just described is carried on an arm 28 that may be moved either linearly or in an x-y plane to position the dispenser at a selected deposition position, as will be described.

Figure 2A:
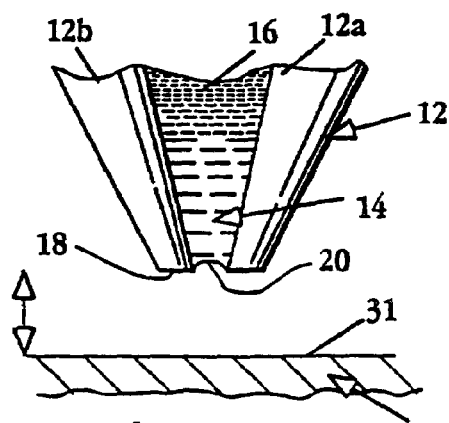
FIGS. 2A-2C illustrate steps in the delivery of a fixed-volume bead on a hydrophobic surface employing the dispensing head from FIG. 1, in accordance with one embodiment of the method of the invention.
Figure 2B:
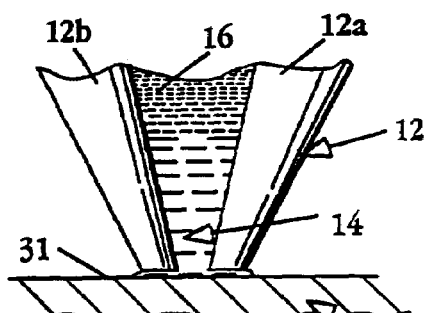
Figure 2C:
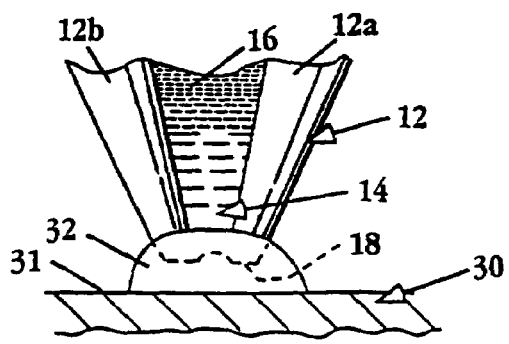

FIGS. 2A-2C illustrate the method of depositing a known amount of solution of a distinct-sequence polynucleotide solution in the just-described dispenser on the surface of a solid support, such as the support indicated at 30. The support is a polymer, glass, or other solid-material support having a surface indicated at 31.

In one general embodiment, the surface is a relatively hydrophilic, i.e., a wettable surface, such as a surface having native, bound or covalently attached charged groups. One such surface described below is a glass surface having an absorbed layer of a polycationic polymer, such as poly-l-lysine.

Initially, the dispenser is loaded with molecules of a selected gene sequence, such as by dipping the dispenser tip, after washing, into a solution of the gene sequence solution, and allowing filling by capillary flow into the dispenser channel. The dispenser is now moved to a selected position with respect to a support surface, placing the dispenser tip directly above the support-surface position at which the polynucleotide solution is to be deposited. This movement takes place with the dispenser tip in its raised position, as seen in FIG. 2A, where the tip is typically at least several (1-5) mm above the surface of the substrate.

With the dispenser so positioned, solenoid 22 is now activated to cause the dispenser tip to move rapidly toward and away from the substrate surface, making momentary contact with the surface, in effect, tapping the tip of the dispenser against the support surface. The tapping movement of the tip against the surface acts to break the liquid meniscus in the tip channel, bringing the liquid in the tip into contact with the support surface. This, in turn, produces a flowing of the liquid into the capillary space between the tip and the surface, acting to draw liquid out of the dispenser channel, as seen in FIG. 2B.

FIG. 2C shows flow of fluid from the tip onto the support surface, which in this case is a hydrophobic surface. The figure illustrates that liquid continues to flow from the dispenser onto the support surface until it forms a liquid bead 32. At a given bead size, i.e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

For liquid-dispensing on a more hydrophilic surface, the liquid will have less of a tendency to bead, and the dispensed volume will be more sensitive to the total dwell time of the dispenser tip in the immediate vicinity of the support surface, e.g., the positions illustrated in FIGS. 2B and 2C.

The desired deposition volume, i.e., bead volume, formed by this method is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip, i.e., the size of the area spanned by the tip, (ii) the hydrophobicity of the support surface, and (iii) the time of contact with and rate of withdrawal of the tip from the support surface. In addition, bead size may be reduced by increasing the viscosity of the medium, effectively reducing the flow time of liquid from the dispenser onto the support surface. The drop size may be further constrained by depositing the drop in a hydrophilic region surrounded by a hydrophobic grid pattern on the support surface.

In a typical embodiment, the dispenser tip is tapped rapidly against the support surface, with a total residence time in contact with the support of less than about 1 msec, and a rate of upward travel from the surface of about 10 cm/sec.

Assuming that the bead that forms on contact with the surface is a hemispherical bead, with a diameter approximately equal to the width of the dispenser tip, as shown in FIG. 2C, the volume of the bead formed in relation to dispenser tip width (d) is given in Table 1 below. As seen, the volume of the bead ranges between 2 pl to 2 nl as the width size is increased from about 20 to 200 μm.

TABLE 1

| d | Volume (nl) |
|---|---|
| 20 μm | $2 \times 10^{-3}$ |
| 50 μm | $3.1 \times 10^{-2}$ |
| 100 μm | $2.5 \times 10^{-1}$ |
| 200 μm | 2 |

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired pl to nl range can be achieved in a repeatable fashion.

After depositing a bead at one selected location on a support, the tip is typically moved to a corresponding position on a second support, a droplet is deposited at that position, and this process is repeated until a liquid droplet of the polynucleotide solution has been deposited at a selected position on each of a plurality of supports.

The tip is then washed to remove the polynucleotide solution, filled with another distinct-sequence polynucleotide solution and this solution is now deposited at another array position on each of the supports. In one embodiment, the tip is washed and refilled by the steps of (i) dipping the capillary channel of the device in a wash solution, (ii) removing wash solution drawn into the capillary channel, and (iii) dipping the capillary channel into the new gene-sequence solution.

The tweezers-like, open-capillary dispenser tip provides the advantages that (i) the open channel of the tip facilitates rapid, efficient washing and drying before reloading the tip with a new, e.g., different-sequence polynucleotide solution, (ii) passive capillary action can load the sample directly from a standard microwell plate while retaining sufficient sample in the open capillary reservoir for the printing of numerous arrays, (iii) open capillaries are less prone to clogging than closed capillaries, and (iv) open capillaries do not require a perfectly faced bottom surface for fluid delivery.

Figure 3:
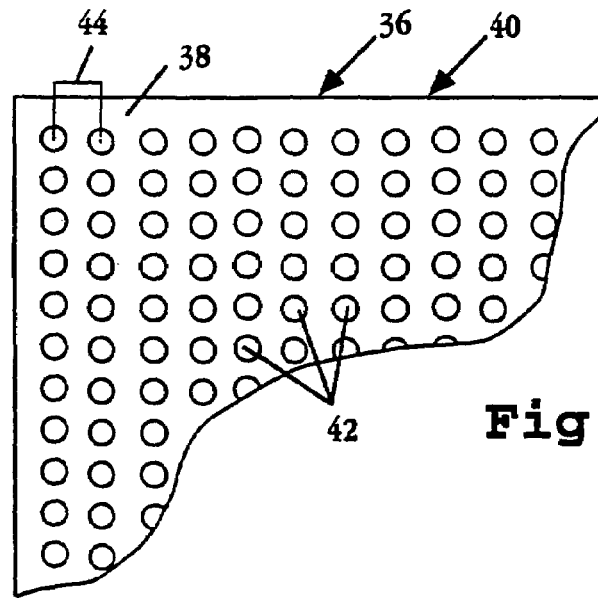
FIG. 3 shows a portion of a two-dimensional array of analyte-assay regions constructed according to the method of the invention.

A portion of a microarray 36 formed on the surface 38 of a solid support 40 in accordance with the method just described is shown in FIG. 3. The array is formed of a plurality of distinct-sequence gene regions, such as regions 42, where each region may include a different gene sequence or different concentration of gene sequence. As indicated above, the diameter of each region is preferably between about 20-200 μm, where each region contains between about 0.1 femtomole to 100 nanomoles of the distinct-sequence polynucleotide.

The spacing between each region and its closest (non-diagonal) neighbor, measured from center-to-center (indicated at 44), is preferably in the range of about 20-400 μm. Thus, for example, an array having a center-to-center spacing of about 250 μm contains about 40 regions/cm or 1,600 regions/cm². After formation of the array, the support is treated to evaporate the liquid of the droplet forming each region, to leave a desired array of dried, relatively flat regions. This drying may be done by heating or under vacuum.

In some cases, it is desired to first rehydrate the droplets containing the polynucleotides to allow for more time for adsorption to the solid support. It is also possible to spot out the polynucleotides in a humid environment so that droplets do not dry until the arraying operation is complete, or to spot out the polynucleotides on a heated surface to increase the rate of absorption.

Figure 4:
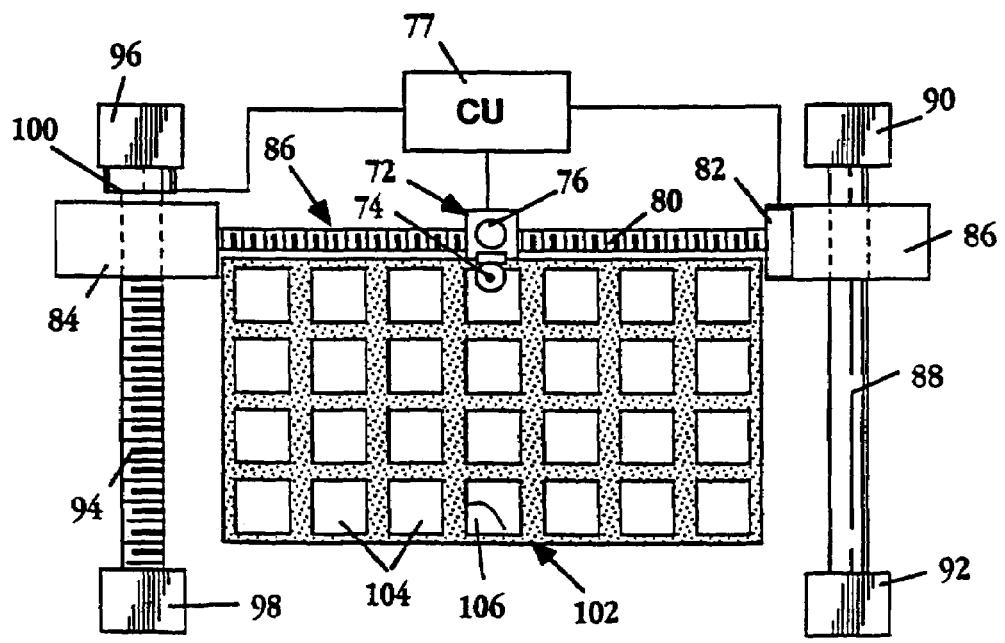
FIG. 4 is a planar view showing components of an automated apparatus for forming arrays in accordance with the invention.

FIG. 4 shows, in simplified form, portions of an apparatus designed to automate production of a large number of microarrays of the types described above. A dispenser device 72 in the apparatus has the basic construction described above with respect to FIG. 1, and includes a dispenser 74 having an open-capillary channel terminating at a tip, substantially as shown in FIGS. 1 and 2A-2C.

The dispenser is mounted in the device for movement toward and away from a dispensing position at which the tip of the dispenser taps a support surface, to dispense a selected volume of polynucleotide solution, as described above. This movement is effected by a solenoid 76 as described above. Solenoid 76 is under the control of a control unit 77 whose operation will be described below.

The dispenser device is carried on an arm 74 which is threadedly mounted on a worm screw 80 driven (rotated) in a desired direction by a stepper motor 82 also under the control of unit 77. At its left end in the figure screw 80 is carried in a sleeve 84 for rotation about the screw axis. At its other end, the screw is mounted to the drive shaft of the stepper motor, which in turn is carried on a sleeve 86. The dispenser device, worm screw, the two sleeves mounting the worm screw, and the stepper motor used in moving the device in the "x" (horizontal) direction in the figure form what is referred to here collectively as a displacement assembly 86.

The displacement assembly is constructed to produce precise, micro-range movement in the direction of the screw, i.e., along an x axis in the figure. In one mode, the assembly functions to move the dispenser in x-axis increments having a selected distance in the range 5-25 μm. In another mode, the dispenser unit may be moved in precise x-axis increments of several microns or more, for positioning the dispenser at associated positions on adjacent supports, as will be described below.

The displacement assembly, in turn, is mounted for movement in the "y" (vertical) axis of the figure, for positioning the dispenser at a selected y axis position. The structure mounting the assembly includes a fixed rod 88 mounted rigidly between a pair of frame bars 90, 92, and a worm screw 94 mounted for rotation between a pair of frame bars 96, 98. The worm screw is driven (rotated) by a stepper motor 100 which operates under the control of unit 77. The motor is mounted on bar 96, as shown.

The structure just described, including worm screw 94 and motor 100, is constructed to produce precise, micro-range movement in the direction of the screw, i.e, along an y axis in the figure. As above, the structure functions in one mode to move the dispenser in y-axis increments having a selected distance in the range 5-250 μm, and in a second mode, to move the dispenser in precise y-axis increments of several microns (μm) or more, for positioning the dispenser at associated positions on adjacent supports.

The displacement assembly and structure for moving this assembly in the y axis are referred to herein collectively as positioning means for positioning the dispensing device at a selected array position with respect to a support.

A holder 102 in the apparatus functions to hold a plurality of supports, such as supports 104 on which the microarrays of regent regions are to be formed by the apparatus. The holder provides a number of recessed slots, such as slot 106, which receive the supports, and position them at precise selected positions with respect to the frame bars on which the dispenser moving means is mounted.

As noted above, the control unit in the device functions to actuate the two stepper motors and dispenser solenoid in a sequence designed for automated operation of the apparatus in forming a selected microarray of different-sequence polynucleotide regions on each of a plurality of supports.

The control unit is constructed, according to conventional microprocessor control principles, to provide appropriate signals to each of the solenoid and each of the stepper motors, in a given timed sequence and for appropriate signalling time. The construction of the unit, and the settings that are selected by the user to achieve a desired array pattern, will be understood from the following description of a typical apparatus operation.

Initially, one or more supports are placed in one or more slots in the holder. The dispenser is then moved to a position directly above a well (not shown) containing a solution of the first solution to be dispensed on the support(s). The dispenser solenoid is actuated now to lower the dispenser tip into this well, causing the capillary channel in the dispenser to fill. Motors 82, 100 are now actuated to position the dispenser at a selected array position at the first of the supports. Solenoid actuation of the dispenser is then effective to dispense a selected-volume droplet of that solution at this location. As noted above, this operation is effective to dispense a selected volume preferably between 2 pl and 2 nl of the polynucleotide solution.

The dispenser is now moved to the corresponding position at an adjacent support and a similar volume of the solution is dispensed at this position. The process is repeated until the solution has been dispensed at this preselected corresponding position on each of the supports.

To dispense the next solution, the dispenser is positioned over a wash solution (not shown), and the dispenser tip is dipped in and out of this solution until the reagent solution has been substantially washed from the tip. Solution can be removed from the tip, after each dipping, by vacuum, compressed air spray, sponge, or the like.

The dispenser tip is now dipped in a second polynucleotide solution well, and the filled tip is moved to a second selected array position in the first support. The process of dispensing solution at each of the corresponding second-array positions is then carried as above. This process is repeated until an entire microarray of reagent solutions on each of the supports has been formed.

Figure 5:
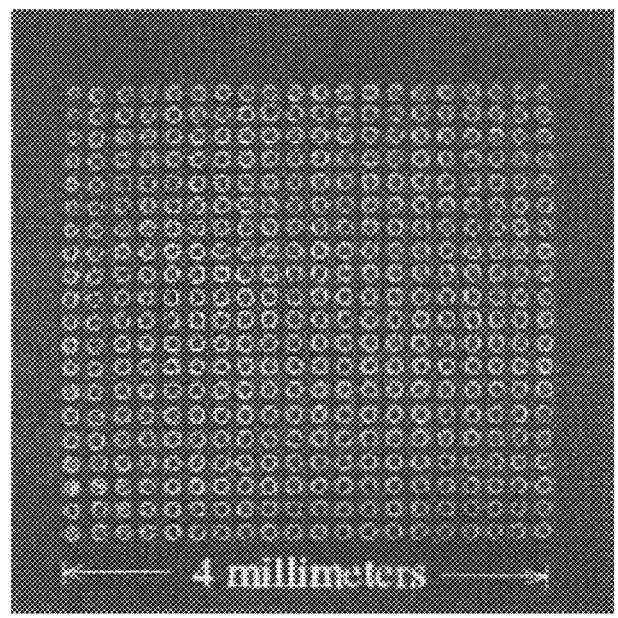
FIG. 5 shows a fluorescent image of an actual 20×20 array of 400 fluorescently-labeled DNA samples immobilized on a poly-l-lysine coated slide, where the total area covered by the 400 element array is 16 square millimeters.

FIG. 5 shows a microarray device of the type useful in practicing the method of the invention. The device includes a glass substrate 138 having formed on its surface, a coating of a polycationic polymer, preferably a cationic polypeptide, such as polylysine or polyarginine. Formed on the polycationic coating is a microarray 140 of distinct sequence polynucleotides, each localized at known selected array regions, such as regions 142.

The slide is coated by placing a uniform-thickness film of a polycationic polymer, e.g., poly-l-lysine, on the surface of a slide and drying the film to form a dried coating. The amount of polycationic polymer added is sufficient to form at least a monolayer of polymers on the glass surface. The polymer film is bound to the surface via electrostatic binding between negative silyl-OH groups on the surface and charged amine groups in the polymers. Poly-l-lysine coated glass slides may be obtained commercially, e.g., from Sigma Chemical Co. (St. Louis, Mo.).

To form the microarray, defined volumes of distinct sequence polynucleotides are deposited on the polymer-coated slide, as described in Section II. According to an important feature of the device, the deposited polynucleotides remain bound to the coated slide surface non-covalently when an aqueous DNA sample is applied to the substrate under conditions which allow hybridization of reporter-labeled polynucleotides in the sample to complementary-sequence (single-stranded) polynucleotides in the substrate array. The method is illustrated in the examples below.

To illustrate this feature, a substrate of the type just described, but having an array of same-sequence polynucleotides, was mixed with fluorescent-labeled complementary DNA under hybridization conditions. After washing to remove non-hybridized material, the substrate was examined by low-power fluorescence microscopy. The array can be visualized by the relatively uniform labeling pattern of the array regions.

In a preferred embodiment, each microarray contains at least $10^3$ distinct polynucleotide or polypeptide biopolymers per surface area of less than about 1 $cm^2$. In the embodiment shown in FIG. 5, the microarray contains 400 regions in an area of about 16 $mm^2$, or $2.5 \times 10^3$ regions/$cm^2$. Also in a preferred embodiment, the polynucleotides in the each microarray region are present in a defined amount between about 0.1 femtomoles and 100 nanomoles in the case of polynucleotides. As above, the ability to form high-density arrays of this type, where each region is formed of a well-defined amount of deposited material, can be achieved in accordance with the microarray-forming method described in Section II.

Also in a preferred embodiment, the polynucleotides have lengths of at least about 50 bp, i.e., substantially longer than oligonucleotides which can be formed in high-density arrays by various in situ synthesis schemes.

III. Identifying Gene Expression Levels

This section describes a method which uses the polynucleotide arrays described above for identification of differential gene expression levels of multiple genes in test and control cells. Such differential gene expression can be determined, for example, between different tissues in an organism, or between samples from the same tissue or cell type in different states, such as activated/non-activated, infected/non-infected, cancerous/non-cancerous, affected/not affected, and diseased/healthy. Cells in these states are collectively referred to as "test" cells (e.g., activated, infected, cancerous, affected, diseased, etc.) and "control" cells (e.g., non-activated, non-infected, non-cancerous, not affected, healthy, etc.). More generally, differential gene expression is determined using cells from a population of test individuals who have a particular condition or disease (test cells), and another population of control individuals who are "normal" for the condition selected, e.g., a disease or infectious condition in the test individuals.

The method employs an array, and preferably a microarray of "target" gene sequences, or polynucleotides, which is then probed with reporter-labeled nucleic acids obtained or derived from the test and control cells. The amount of reporter-labeled nucleic acid that hybridized at each position in the microarray is determined. This signal reflects the amount or relative number of reporter-labeled nucleic acid fragments in the hybridization mixture that have a nucleotide sequence that is effective to hybridize with the nucleotide sequence of the immobilized target gene or fragment. Accordingly, if a particular messenger nucleic acid is represented at a relatively high level in the hybridization mixture, it will give a strong hybridization signal (high reporter level) at the position of an immobilized target having a sequence that is homologous to the complement of the reporter-tagged nucleic acid sequence.

The pattern of reporter signals may be quantitated and analyzed on a computer. As described below, the levels of gene expression, as determined by reporter levels bound to the genes in the array, are determined for a population of test or control individuals, to provide a statistical measure of genes in the array which are expressed at above- or below-normal values in test individuals.

A. Fabrication of Array

An array, such as a microarray, of immobilized target gene sequences is fabricated as described above. The DNA used in fashioning the array may be obtained from any of a variety of sources. Preferably, the array contains at least $10^3$ distinct gene sequences per $cm^2$ surface area. The array contains at least $10^2$ distinct gene sequences, and preferably $10^3$-$10^4$ distinct sequences.

The DNA at each location in the array has a unique nucleotide sequence, which may be known or unknown. For example, a genomic library can be constructed from DNA from which repetitive sequences have been self-hybridized-out. Alternatively, such a library may be purchased from commercial sources, such as Clontech (Palo Alto, Calif.). Clones from the library may be spotted on a substrate to fashion a set of arrays which includes all of the unique sequences represented in the library.

Clones from cDNA libraries may also be spotted onto a substrate to generate a microarray. Methods for the construction of cDNA libraries from a variety of tissues are well known in the art (Maniatis, et al., Ausubel, et al., Sambrook, et al.). Further, cDNA libraries may be conveniently obtained from several commercial sources, including Clontech (Palo Alto, Calif.) and Stratagene (La Jolla, Calif.).

Arrays may also be made with expressed sequence tags (ESTs) derived from various tissues (e.g., Orr). A set of arrays can be made for each tissue for which there exist ESTs, or a more general set of ESTs derived from two or more tissues can be prepared, depending on the application.

In a general embodiment of the invention, ESTS, or EST genes from multiple tissue sources are spotted onto a substrate to generate an array. Preferably, the array includes at least $10^3$ such EST genes. The EST genes in the plasmid vectors are amplified using primers directed against regions of the plasmid flanking the inserts. The amplified DNAs are purified with PCR clean-up kits (Quiagen, Chatsworth, Calif.), and spotted to generate an array as described above. An exemplary source of ESTs is the Merck-Washington University Consortium for ESTs (Merck and Co., Whitehouse, N.J.), as well as through the Image Consortium of Lawrence Livermore Labs (Livermore, Calif.).

Each distinct gene sequence (e.g., single library clone or EST) is preferably disposed at a separate, defined position in the array and is present in a defined amount, typically between about 0.1 femtomole and 100 nanomoles. The spotting, or application of the DNA to the substrate, may be done in duplicate to provide a measure for the consistency of the assay and validity of the results.

Following the spotting, the slides are typically rehydrated in a humid chamber for about 2 hours, snap dried on a hot plate at 100° C., rinsed to remove un-absorbed DNA, denatured, UV-crosslinked and treated with succinic anhydride as described in Example 1. The rehydration and snap drying are performed to facilitate the-formation of a uniform, as opposed to an annular, distribution of the dried DNA. In another embodiment of the method, the DNA is spotted onto heated glass surface, which eliminates the rehydration and snap-drying steps and may achieve a similar uniform distribution of DNA.

B. Test Individuals Having a Shared Phenotype

Reporter-labeled copies of messenger nucleic acids, or fragments, are prepared from cDNAs or mRNAs obtained from "test" and "control" sources. As indicated above, the test sources are typically individuals (test individuals) having a shared phenotype that is not present in control individuals. Examples of such a phenotype include a pathogenic infection, such as a viral, bacterial or parasitic infection; a disease, such as a cancer, heart disease, diabetes, AIDS, an autoimmune disease, allergy, asthma, cardiovascular condition, various genetic diseases, degenerative diseases, and the like; and a predisposition to a disease or condition, such as a predisposition to heart disease, hypertension, diabetes, weight gain, stroke, neurodegenerative disease, psychiatric disease, and other diseases or conditions with an inheritable risk factor.

The shared phenotype may also include, for example, exposure to a known therapeutic agent or treatment modality, e.g., x-irradiation, or exposure to known environmental factors, e.g., a suspected factor in the workplace.

The control sources can be individuals (control individuals) who are "normal" for the test phenotype, i.e., individuals who are not affected with the disease or condition for which it is desired to construct a subarray, or any standard nucleic acid sample that provides a standard, reproducible hybridization signal at each array element.

C. Test Cells and Control Cells

The test and control cells used as a source for the reporter-labeled copies of messenger nucleic acids, or fragments, are typically those cells that are directly affected by the disease or condition for which it is desired to generate a subarray of the present invention.

As examples, for use in constructing a subarray of genes whose gene expression levels are specifically related to a specific tumor condition, the test cells may be neoplastic cells, and the control cells, non-neoplastic cells of the same type.

For use in constructing a subarray of genes whose gene expression levels are specifically related to a genetic disease, the test cells may be cells from a tissue whose functioning is affected by the disease, and the control cells, cells from the same tissue in a normal individual.

For use in constructing a subarray of genes whose gene expression levels are specifically related to a virus-infected cell, the test cells may be virus-infected cells, and the control cells, uninfected cells of the same cell type from a non-infected individual.

For use in constructing a subarray of genes whose gene expression levels are specifically related to immune cells under immunological challenge, the test cells may be immunologically challenged immune cells, and the control cells, non-challenged immune cells of the same cell type.

For use in constructing a subarray of genes whose gene expression levels are specifically related to drug response in a given test cell type, the test and control cells may be the same cell type, in the presence and absence of the drug.

The invention also contemplates the use of cells other that those directly affected by the disease or condition as a source of test and control cells. Using the above liver tumor example, if it is suspected that certain genes in peripheral blood cells are upregulated or downregulated as a result of a liver tumor, the test cells for generating a subarray of liver tumor regulated genes may be peripheral blood cells from an individual having a liver tumor, and the control cells peripheral blood cells from a normal individual, e.g., peripheral blood lymphocytes.

D. Preparation of Reporter-labeled Nucleic Acid

Reporter-labeled copies of messenger nucleic acid fragments are prepared from cDNAs or mRNAs obtained from "test" and control sources. Messenger RNA, e.g., polyA RNA, may be reporter labeled by conventional methods, e.g., where the label is introduced at preferably the 5' or 3' end of the mRNA by suitable terminal transferase enzymes in the presence of fluorescent labeled nucleotides. cDNA may be reverse-transcribed from mRNA isolated from test and control cells, and may be used directly in reporter-labeled form, where the label is preferably introduced through the use of labeled nucleotides during reverse transcription and/or second-strand synthesis. Alternatively, the cDNA formed may be amplified by PCR or may be may be obtained from cDNA libraries that were generated from test and control cells. In cases where the reporter-labeled copies of messenger nucleic acid is obtained from a cDNA library, it is nevertheless considered to be "obtained" from the cell or tissue from which the library was made.

Messenger nucleic acids, or fragments, from the test and control cells may be labeled with different reporter moieties that can be independently detected with a minimum of signal cross-contamination. In one embodiment of the invention, the two sets of reporter-labeled messenger nucleic acids, corresponding to test and control cells, are hybridized simultaneously to an array containing at least $10^2$ immobilized DNA fragments, each having a different nucleotide sequence. As is described more fully below, signals from the two reporter moieties may be detected either simultaneously or sequentially. Once normalized, the relative intensity of the signals reflects differences in the level of gene expression between the test and control cells.

Test and control cells suitable for the preparation of reporter-labeled copies of nucleic acid may be obtained directly from "test" and "control" individuals (e.g., as a tissue biopsy or blood sample), or they may be obtained from cell or tissue culture banks. Of course, cells that had been frozen or otherwise preserved may also be a suitable source of polynucleotides for the preparation of reporter-labeled messenger nucleic acid fragments.

Methods for the isolation of RNA and/or mRNA from cells or tissue, as well as for reverse transcription of mRNA into cDNA, are well known (e.g., Ausubel, et al.). In one embodiment of the invention, reporter-labeled nucleic acid is prepared during the reverse-transcription of mRNA into cDNA by substituting one of the four deoxynucleotides (A, C, T or G) with a reporter-labeled analogue of that deoxynucleotide. For example, the reaction can be carried out as described in Example 1, below, using fluorescein-12-dCTP (or lissamine-5-dCTP).

Reporter-labeled messenger nucleic acids may also be prepared by 5' or 3' end-labeling existing cDNA fragments (e.g., inserts of clones from a cDNA library) with a reporter moiety using known methods (e.g., Ausubel).

A number of different reporters may be employed, though the final detectable moiety on the reporter is preferably fluorescent. As discussed above, nucleotides having a fluorescent moiety attached are commercially available.

Fluorescence-based detection has several advantages over other types of reporter systems. For example, fluorescent signals do not scatter, permitting a closer spacing of the cDNA elements relative to spacing that could be achieved using radioactive or chemiluminescent detection methods. Furthermore, fluorescent signals can be multiplexed using different fluorophores for simultaneous detection of many hybridization reactions on the same array.

In certain cases, it may be desirable to use a fluorescently-labeled secondary reporter molecule that recognizes a primary molecule incorporated into or derivatized to the copies of messenger nucleic acid. A number of such systems are available. The most commonly used are biotin and digoxigenin. Either label can be easily incorporated into DNA probes and be detected using fluorochromes, which are available directly conjugated to anti-digoxigenin antibodies and to avidin. Kits for performing such labeling reactions are available, e.g., from Amersham (Arlington Heights, Ill.) and Boehringer-Mannheim (Indianapolis, Ind.).

The fluorescent detection moieties of the reporter system are preferably selected to have excitation maxima at a wavelength where the excitation light source can provide a strong excitation. For example, the system described in Example 1, below, employs a mixed gas multiline 10 W laser that generates spectral lines at a number of wavelengths including 488 nm and 568 nm. These wavelengths are near the excitation maxima of the two fluorophores used (494 nm for fluorescein and 570 nm for lissamine.

Figure 6:
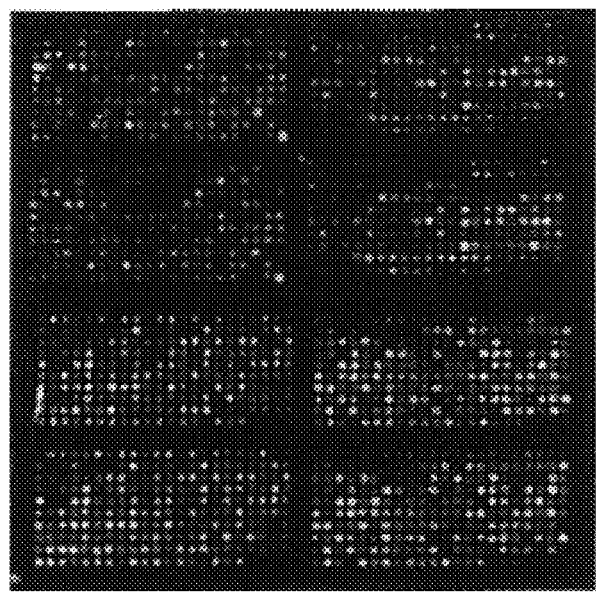
FIG. 6 is a fluorescent image of a 1.8 cm×1.8 cm microarray containing lambda clones with yeast inserts, the fluorescent signal arising from the hybridization to the array with approximately half the yeast genome labeled with a green fluorophore and the other half with a red fluorophore.

As suggested above, fluorescence detection also allows for simultaneous determination of test and control expression levels on a single microarray. In this embodiment, test and control nucleic acids are labeled with different fluorescent reporters, and expression levels of each is measured independently on the array. The ability to independently monitor differently labeled nucleic acids on a microarray is illustrated in FIG. 6. The figure shows the hybridization pattern of the two yeast chromosome pools hybridized to an array of lambda clones with the inserts. A red signal in the figure indicates that the clone on the array surface originates from one of the largest six yeast chromosomes. A green signal indicates that the lambda clone originates from one of the smallest ten yeast chromosomes. Orange signals indicate repetitive sequences which cross hybridize to both chromosome pools. Control spots on the array confirm that the hybridization is specific and reproducible.

E. Hybridization of Reporter-labeled Nucleic Acid to the Array

Hybridization of reporter-labeled nucleic acid to the array of immobilized target gene sequences is carried out using standard methods (e.g., as described in Maniatis, et al., Sambrook, et al., Ausubel, et al.) taking into account any special circumstances of a particular hybridization reaction. Typical hybridization conditions are given in Example 1. Such hybridization conditions are effective to hybridize the reporter-labeled nucleic acid to complementary-sequence target genes immobilized on the array.

Special circumstances relating to hybridization reactions employed in the practice of the invention include, for example, cases where the array is a microarray (e.g., a 5 cm$^2$ or smaller array) and benefits from small hybridization volumes (e.g., about 10 µl). Such a microarray spotted on, e.g., a glass slide, can be hybridized by placing the hybridization solution under a coverslip, and performing the hybridization in a humidified chamber, such as described in Example 1.

It will be appreciated that the level of reporter detected at any array position is directly related to the relative concentration of a particular-sequence reporter-labeled nucleic acid in the total mixture of reporter labeled copies of nucleic acids, i.e., the relative number of molecules of that nucleic acid species. Since the level of gene expression is related to the number of mRNA copies obtained from the test and control cells, and therefore to the number of cDNA copies produced from the mRNA species, the relative reporter level at each position on the array is directly related to the level of gene expression of that sequence in the test or control cells.

One important feature of the present invention, where the method is carried out using a gene microarray, is that volume of cell-derived cDNA material applied to array can be as little as 1-10 µl. For example, if a hybridization volume of 10 µl is used with a total of about 10 µg reporter-labeled cDNA, transcripts as rare as 1 part in 50,000 are detectable with fluorescent detection, without the requirement of amplifying the nucleic acid copies prior to hybridization. This ensures that the reporter levels measured at each position on the array reflect actual mRNA concentrations without severe distortions that may be introduced by PCR amplification or using cloned cDNA species as a source of reporter-labeled nucleic acids.

Experiments performed in support of the present invention have demonstrated good quantitation can be achieved on a microarray using 2 µl hybridization volumes and 2 µg reporter-labeled cDNAs.

Figure 7A:
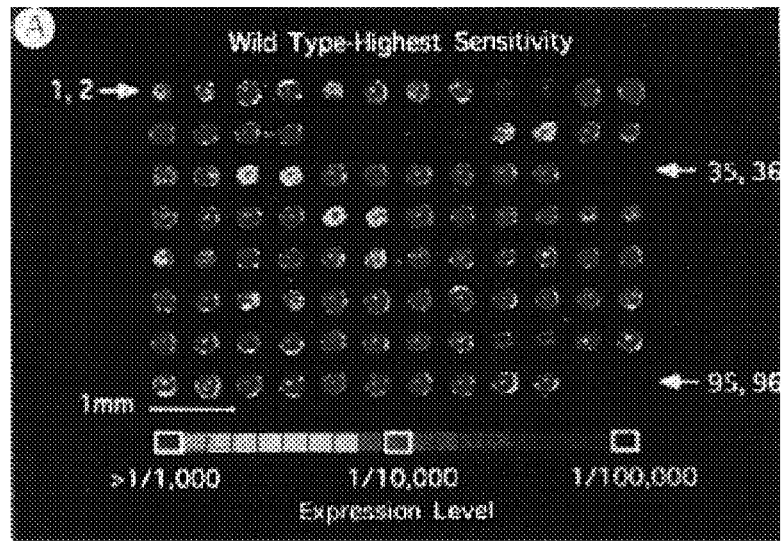
FIGS. 7A and 7B show scans of hybridization signals from an array of genes probed with fluorescently-labeled *Arabidopsis* cDNA at high (7A) and intermediate (7B) photomultiplier tube settings.
Figure 7B:
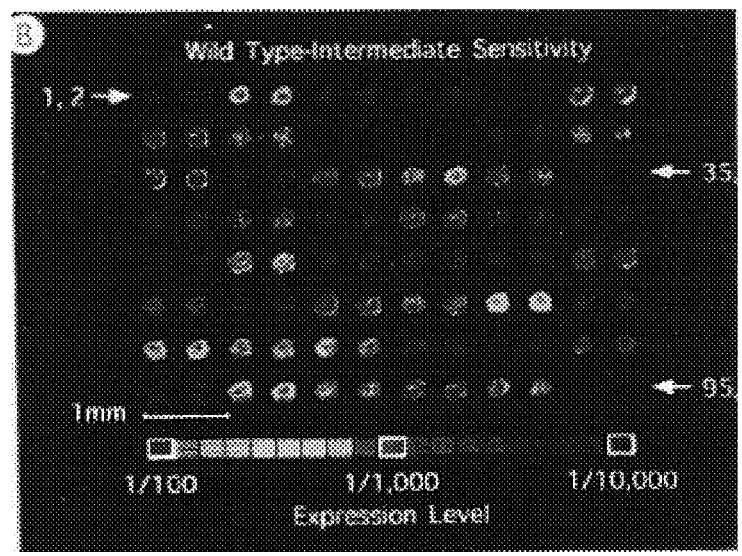

The specificity, lack of cross hybridization, and ability to detect expression at a 1:50,000 level in the method is illustrated in FIGS. 7A and 7B, which show the fluorescent scans of the same array in a pseudocolor scale that was calibrated to reflect expression levels. Calibration of expression was performed using human acetylcholine receptor mRNA added to the *Arabidopisis* total poly-A mRNA prior to reverse transcription at a weight dilution ratio of 1:10,000 (arrays elements 1,2). Other *Arabidopisis* genes on the array whose expression levels were known from Northern analysis were also used for calibration purposes.

FIG. 7A is a scan of the array at a high photomultiplier tube setting for detection of rare transcripts down to a molar dilution ratio of as low as 1:100,000. It will be appreciated that adjacent dots (representing duplicate spots of the same cDNA clone) typically appear nearly identical in intensity, confirming the reproducibility of the spotting and immobilization procedures. Despite the high sensitivity setting used in this image, the negative controls (Yeast TRP4 at 95, 96; rat glucocorticoid receptor gene at 35, 36) did not produce a detectable signal. Note that the human acetylcholine receptor gene (1,2) produced a clear signal at a w/w dilution of 1:10,000.

FIG. 7B is a scan of the same array at a lower photomultiplier tube setting (intermediate sensitivity; detection of one in 10,000) to unsaturate the signals of the more highly expressed genes on the array. This setting allows a linear detection of more abundant transcripts. Quantitation of both scans revealed a detectable range of expression levels spanning three orders of magnitude for the 45 genes tested. Details of the method are given in Example 1.

F. Detecting Hybridized Sequences

Following hybridization and washes at selected stringencies, the pattern of reporter levels for nucleic acids from the test cells is compared with that of nucleic acids from the control cells. The method used for detection of reporter levels, of course, depends on the reporter employed. Radioisotope reporters may be detected using, for example, autoradiography film or a "PHOSPHORIMAGER" (Molecular Dynamics, Sunnyvale Calif.). A "PHOSPHORIMAGER" can generate images similar to those shown, for example, in FIGS. 6A and 6B. Similarly, chemiluminescent reporters can be detected using photographic film, while calorimetric reporters can be detected by eye and documented using a standard film camera or optical document scanner. The developed film images can be scanned into a microcomputer using commercially-available equipment and software, and analyzed.

The detection methods mentioned in the above paragraph typically have significantly lower spatial resolution than can be achieved using a fluorescence-based system. This limitation is not necessarily serious when the array being scanned is relatively large (e.g., a standard format 96-well or 384-well plate). However, when the array being analyzed is a microarray, it is preferable to use a fluorescence-based system.

An exemplary fluorescence-based system is described with respect to Example 2. The system uses a mixed gas laser as a light source, and has a computer-controlled X-Y stage for scanning the array in a raster fashion over a microscope objective. Standard excitation and emission filters are employed to analyze signals from different fluorophores. The fluorescence signals are collected using photomultiplier tubes, whose output can be conveniently digitized using an analog-to-digital (A/D) converter board in a microcomputer.

Fluorescence scanners such as is described are also available commercially. The scanner used in the experiments reported below is similar to the "Gene Chip Scanner" made by Affymetrix (Santa Clara, Calif.).

G. Analysis of Reporter Levels

The data obtained with the reporter detection device is analyzed to compare the pattern of reporter levels for nucleic acids from the test cells with that of nucleic acids from the control cells. Preferably, the fluorescence data are obtained in numerical form, such as from a photomultiplier tube connected to an A/D converter (e.g., as described in Example 1).

The data are typically stored, processed and/or further analyzed on a microcomputer. Typical processing includes displaying the data in a graphical form representing an image of the entire array, with signal amplitude represented by the brightness and/or color at the corresponding location in the array. FIGS. 7A, 7B, 8A, 8B, and 9A and 9B all show such "pseudocolor" images of the relative signal intensity at specific locations in a microarray.

Figure 8A:
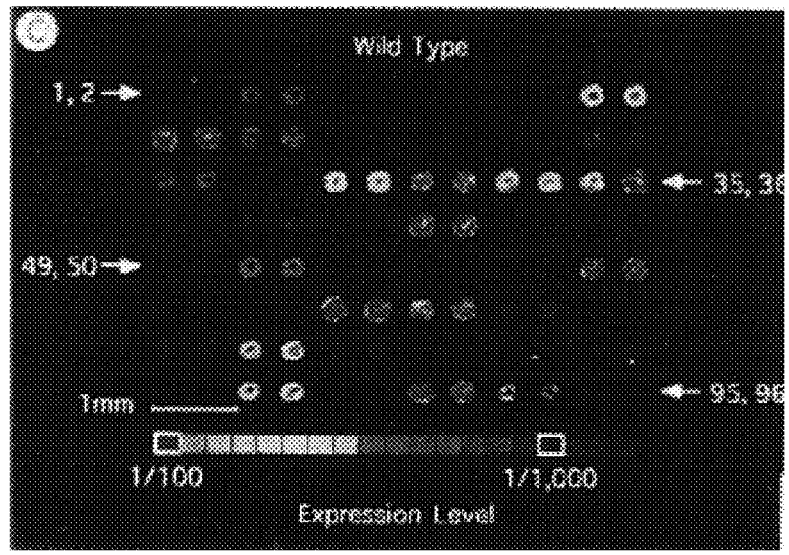
FIGS. 8A and 8B show scans of hybridization signals from an array of genes probed with fluorescently-labeled *Arabidopsis* wild-type (8A) or transgenic HAT4 (8B) cDNA at low photomultiplier tube settings.
Figure 8B:
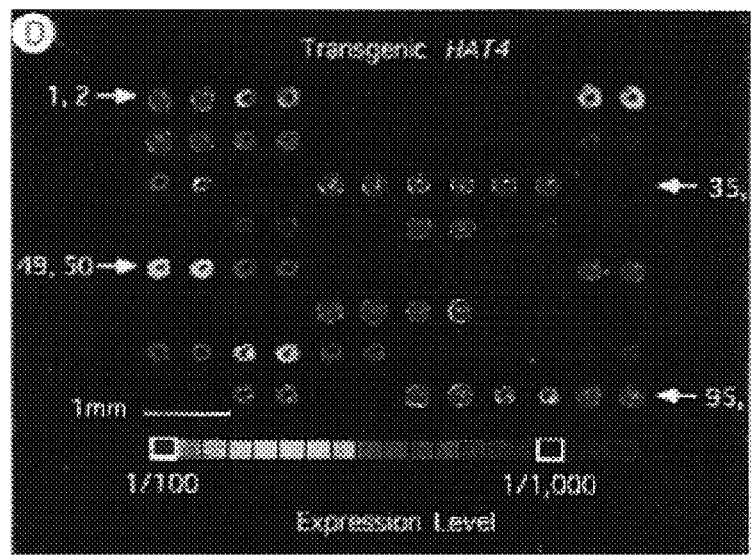

FIGS. 8A and 8B show the detectable differences in gene expression between wild-type tissue labeled with one fluorophore, and transgenic tissue labeled with a second fluorophore, determined at an intermediate-sensitivity (1:10,000) fluorescein scan of the cDNA array corresponding to the hybridization pattern of the wild-type *Arabidopsis* total cDNA. No detectable signal was observed from array elements 49, 50, and 1,2, indicating a lack of HAT4 expression and acetylcholine gene hybridization (acetylcholine gene DNA was added to match the HAT4 expression level). The positive control (rat glucocorticoid receptor gene; elements 35,36) showed a positive hybridization signal, while the negative control (the yeast TRP4 gene; elements 95,96) showed a lack of hybridization signal.

FIG. 8B shows a matched-intensity lissamine scan of the same cDNA array corresponding to the hybridization pattern of the transgenic *Arabidopisis* total cDNA. Both HAT4 (elements 49,50) and the acetylcholine gene (elements 1,2; added to roughly match the HAT4 expression levels) showed strong hybridization signals. The positive control (the yeast TRP4 gene; elements 95,96) also had a strong signal, whereas the negative control (the glucocorticoid receptor gene; elements 35,36) had no detectable signal at this sensitivity setting.

Figure 9A:
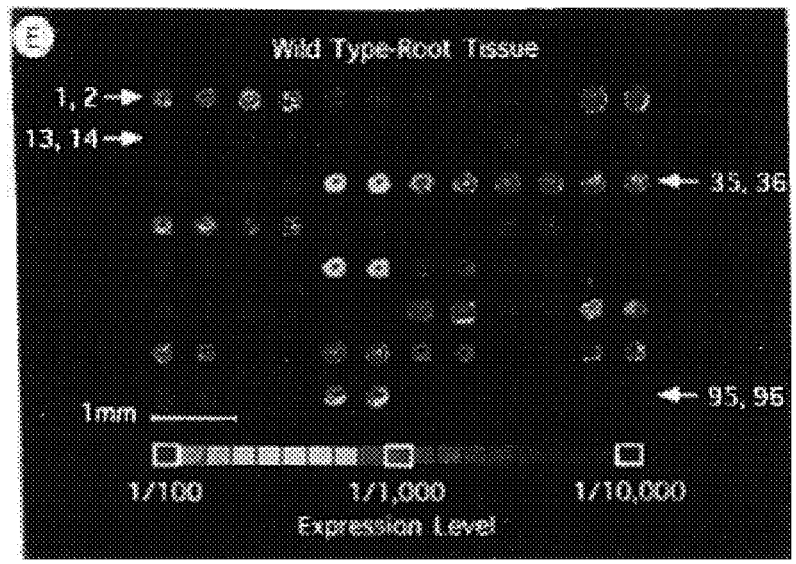
FIGS. 9A and 9B show scans of hybridization signals from an array of genes probed with fluorescently-labeled *Arabidopisis* wild-type root (9A) or wild-type leaf (9B) cDNA at intermediate photomultiplier tube settings.
Figure 9B:
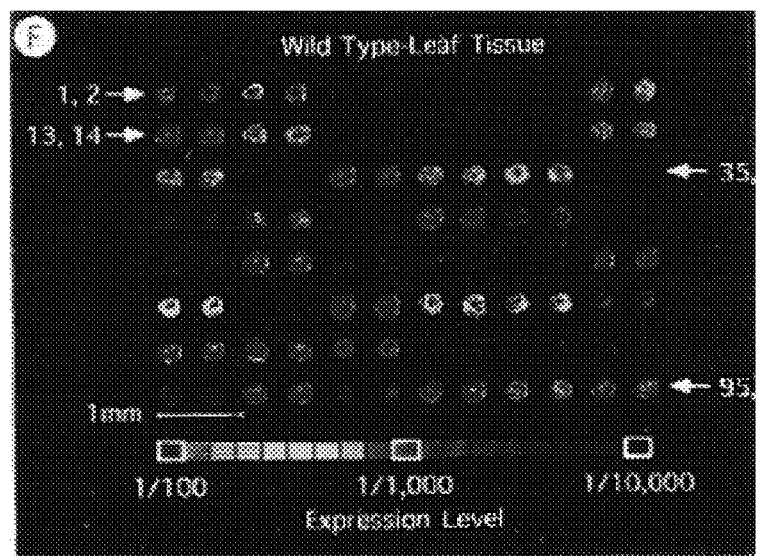

FIGS. 9A and 9B illustrate the ability of the method to determine complex gene patterns of expression in test and control cDNA mixtures. FIG. 9A shows a fluorescein scan of the cDNA array corresponding to the hybridization pattern of root tissue cDNA. FIG. 9B shows a matched-intensity lissamine scan of the same cDNA array corresponding to the hybridization pattern of leaf tissue cDNA. The fluorescence intensities from the acetylcholine receptor gene (elements 1,2) on both arrays were matched by adjusting the photomultiplier tube settings.

The ratio of the fluorescence intensities of the two fluorophores in each spot provides a measure of the differential expression of that gene in leaf versus root tissues. Note the higher levels of expression of the photosynthesis-related chlorophyll binding protein in leaf versus root (elements 13, 14). Note also that other *Arabidopisis* genes were discovered to be more highly expressed in leaf than in root (e.g., element 91, 92) and, conversely, some genes were discovered to be more highly expressed in root than leaf (e.g., element 89, 90). Overall, 26 genes displayed greater than 5-fold differences in expression between control and test tissues.

The average or integrated value corresponding to the total signal from each region of the array is stored in a database for additional analyses. An exemplary additional analysis is the averaging of information obtained from a population of test individuals having a shared phenotype. Due to variations in the genetic make-up of unrelated individuals in a heterogeneous society, differences in the expression of a gene between any two individuals may or may not be significant. If such differences persist in a comparison of the averaged gene expression patterns from the two populations, it becomes more likely that the expression of that particular gene is related to the shared phenotype of the test individuals.

Further, it will be understood that the larger the number of individuals tested, the more significant the remaining differences in gene expression become. Standard statistical analyses may be applied to determine when the messenger nucleic acids from a sufficient number of individuals have been evaluated for differences in gene expression. Typically, samples from at least 5, and preferably 20-50 different test individuals are assayed to obtain statistically meaningful data showing a significant elevation or reduction in reporter levels, when compared with control levels.

It will also be appreciated that the control expression levels for a particular array may be assayed with one population, and those control values can be used as a basis for comparison with a variety of test values, corresponding to different shared phenotypes, as long as no individuals in the control group exhibited any of the phenotypes for which that control is used as a reference.

In a preferred method of practicing the invention, microarrays for each of a number of test individuals are used to establish an "average" test pattern of gene expression levels for the genes on the microarray. similarly, microarrays for each of a number of control individuals are used to establish an "average" control pattern of gene expression levels for the genes on the microarray. The test average pattern is then compared with the control average pattern, to identify those test genes which show significantly, typically at least 2 fold and up to 100 fold or more, increase or decrease in gene expression level with respect to control levels for the same gene.

Alternatively, average test and/or control levels of expression of genes on a microarray can be determined by combining equal amounts of reporter-labeled copies of messenger nucleic acids from each individual from a population of test or control individuals, and determining reporter levels associated with each gene on a single test array or a single control array (which may be the same as the test array).

The method just described takes advantage of the fact that even a single mutated gene or gene product, as well as a drug or other exogenous element, can have a large positive or negative effect on the expression levels of other genes in the organism, which can be detected and quantified using the methods detailed above.

No prior knowledge of the function of individual gene sequences is required in order to establish a correlation between a phenotype and gene expression pattern using the above methods. Rather, numerous hybridizations from individuals sharing a common phenotype are analyzed in a statistical fashion in order to establish a correlation. The correlation can be used for diagnostic purposes and/or monitoring of disease treatment, as will now be described.

IV. Subarray Device and Method

In another aspect, the invention includes a gene-array or subarray device and method of using the device to detect and/or monitor a disease condition.

The device includes a substrate and a subarray of genes which each show a statistically significant increase or a statistically significant decrease, typically at least 2 fold and up to 100 fold or more, in average gene level expression when compared with the average level of gene expression in a control cell type.

The genes in the device are those identified as showing a significant elevation or reduction in reporter levels in test cells, when compared with control-cell levels (Section III). Thus, for example, in constructing a gene-array device for detecting and treatment monitoring a given genetic disease, the method described in Section III is used to identify, from a population of individuals with the genetic condition, those genes which show above- or below-average expression levels. These genes are then selected for use in the gene-array device.

The device itself may be constructed using the polynucleotide array-forming methods outlined in Section II. It is noted, however, that high density polynucleotide spotting is less important in this application, since many fewer genes will typically be required. Ideally, the number of genes whose expression levels correlate with a particular gene condition or treatment method will be between about 5-50, although fewer or more genes may be involved.

Therefore the device, particularly in a microarray format, may include other gene regions, such as gene sequences that are not affected by the condition of interest, for use in establishing and normalizing to control levels of gene expression, or arrays designed for simultaneous detection of several different disease states.

In practicing the method, reporter-labeled copies of messenger nucleic acid are obtained from test cells associated with the physiological state or disease condition from an individual, as described above. The nucleic acid species from the test individual are then contacted with the gene-array device of the invention, whose genes are characterized by a statistically significant increase or decrease in gene expression level, when compared with the level of gene expression of the same gene in control cells. This contacting is carried out under conditions effective to hybridize the nucleic acid species to complementary-sequence genes in the array, similar to the hybridization conditions employed in the method detailed in Section III.

The levels of reporter associated with the genes in the subarray are quantitated, as above, allowing for the determination of a pattern of gene expression levels for the genes on the subarray device. In graphic representation, the pattern can take the form of a pattern of different colors, corresponding to different reporter levels and/or a pattern of different intensities of the same color. In digital form, the pattern may take the form of positive and negative digitized values, measured, for example, with respect to a zero-value control level. The control sample for the subarrays, if one is used, can be any reporter-labeled nucleic acid sequence that provides a standard, reproducible hybridization signal at each array element.

The test pattern is then compared to a diagnostic pattern generated preferably as the average pattern of a number of individuals known to have the diagnostic condition of interest. This average pattern can be constructed as above, either from a plurality of individual array patterns on the subarray device, or as the pattern of pooled nucleic acids samples from several test individuals.

Disease states can be identified, diagnosed and treatments monitored using such gene expression information. For example, patterns of gene expression triggered by mutations in oncogenes and tumor suppression genes can be used to characterize various cancers (Diamandis). Autoimmune diseases can, in part, be characterized according to the activation pattern of gene expression encoding the amplifying and proinflammatory cytokines (Osterland).

Further, subarrays of the present invention generated using the methods detailed herein may be used in drug development applications to measure differential gene expression patterns of trial patient samples in response to drug candidates. Drug candidates that exhibit the desired effect on the genes of interest can be used as the basis of further drug design in a combinatorial or iterative drug development process. Once a drug is fully developed, the effectiveness of treatment for individual patients can be determined by hybridizing a patient's cDNA sample to microarrays containing the same genes used in the drug development process.

In one application, an array of cDNA clones representing genes is hybridized with total cDNA from an organism to monitor gene expression for research or diagnostic purposes. Labeling total cDNA from a normal cell with one color fluorophore and total cDNA from a diseased cell with another color fluorophore and simultaneously hybridizing the two cDNA samples to the same array of cDNA clones allows for differential gene expression to be measured as the ratio of the two fluorophore intensities. This two-color experiment can be used to monitor gene expression in different tissue types, disease states, response to drugs, or response to environmental factors. An example of this approach is illustrated in Examples 2, described with respect to FIGS. 8A and 8B.

The following examples illustrate, but in no way are intended to limit, the present invention.

MATERIALS

Buffers
SSC (sodium chloride/sodium citrate), 20×
3 M NaCl (175 g/liter)
0.3 M Na$_3$citrate-2H$_2$O (88 g/liter)
pH adjusted to 7.0 with 1 M HCl

EXAMPLE 1

Single-Color Fluorescence Detection of Gene Expression Patterns Using Micro Arrays of *Arabidopisis* cDNA Clones A. Generation of Target DNA Fragments Target messenger nucleic acid DNA fragments were made by amplifying the gene inserts from 45 different *Arabidopsis thaliana* cDNA clones and 3 control genes using the polymerase chain reaction (PCR; Mullis, et al.). The DNA fragments comprising the PCR product from each of the 48 reactions were purified using "QIAQUICK" PCR purification kits (Qiagen, Chatsworth, Calif.), eluted in ddH$_2$O, dried to completion in a vacuum centrifuge and resuspended in 15 µl of 3× sodium chloride/sodium citrate buffer (SSC). The capacity of the "QIAQUICK" purification kits is 10 µg of DNA; accordingly, each sample contained about 10 µg or less of DNA.

The samples were then deposited in individual wells of a 96 well storage plate with each sample split among two adjacent wells as a test of the reproducibility of the arraying and hybridization process.

B. Fabrication of Microarray

The samples were spotted on poly-l-lysine-coated microscope slides (Sigma Chemical Co., St. Louis, Mo.) using the automated apparatus described above. The open-capillary printing tip loaded approximately 1 µl of each sample directly from the 96 well storage plates and deposited a 20 nl spot on each of 48 slides. The process was repeated for all 96 wells of the storage plate with the spots on the each slide spaced about 500 µm apart.

After the spotting operation was complete, the slides were rehydrated in a humid chamber for 2 hours, snap dried on a hot plate at 100° C. for 15 seconds, rinsed in 0.1% SDS to remove un-absorbed DNA, denatured in 90° C. distilled water for 2 minutes and ultra-violet (UV)-crosslinked using a "STRATALINKER" (Stratagene, La Jolla, Calif.) set to a total (integrated) energy of 60 mJ. The samples were then treated with 0.1% succinic anhydride in a solution containing 50% N-methyl-pyrrolidinone and 50% 0.1 M Na borate buffer (pH 8.0) for 10 min to reduce non-specific adsorption of the labeled hybridization probe to the poly-l-lysine coated glass surface. The slides were rinsed in distilled water, air dried, and stored.

The positions of several specific elements in the 96-element array, and the reasons for their inclusion, are indicated in Table 1, below. The remaining elements of the array consist of known or unknown genes selected from an *Arabidopisis* cDNA library.

TABLE 1

| Element # | Name | Purpose |
|---|---|---|
| 1, 2 | Human acetylcholine receptor gene | Control for expression level |
| 13, 14 | Chlorophyll binding protein gene | Gene with known expression |
| 35, 36 | Rat glucocorticoid receptor gene | Positive and negative control |
| 49, 50 | HAT4 transcription factor gene | Gene with known expression |
| 95, 96 | Yeast TRP4 gene | Positive and negative control |

C. Preparation of Reporter-labeled Messenger Nucleic Acid

The ability of the invention to monitor absolute, single-gene expression levels was investigated using a single-color fluorescently labeled nucleic acid sample hybridized to the *Arabidopisis* cDNA microarray fabricated as described above.

Total RNA was isolated from plant tissue of *Arabidopisis* using standard methods (Sambrook, et al.). PolyA+ mRNA was prepared from total RNA using "OLIGOTEX-DT" resin (Qiagen). Reverse transcription reactions were carried out using a "STRATASCRIPT"RT-PCR kit (Stratagene) modified as follows: 50 µl reactions contained 0.1 µg/µl *Arabidopisis* mRNA, 0.1 ng/µl human acetylcholine receptor mRNA, 0.05 µg/µl oligo-dT (21mer), 1× first strand buffer, 0.03 units/µl RNase block, 500 µM dATP, 500 µM dGTP, 500 µM dTTP, 40 µM dCTP, 40 µM fluorescein-12-dCTP (or lissamine-5-dCTP) and 0.03 units/µl "STRATASCRIPT" reverse transcriptase. Reactions were incubated for 60 minutes at 37° C., precipitated with ethanol, and resuspended in 10 µl TE.

The samples were then heated for 3 minutes at 94° C. and chilled on ice. RNA was degraded by adding 0.25 µl 10N NaOH followed by a 10 minutes incubation at 37° C. The samples were neutralized by adding 2.5 µl 1M Tris-HCl (pH 8.0) and 0.25 µl 10N HCl, and precipitated with ethanol. Pellets were washed with 70% ethanol, dried to completion in a "SPEED VAC" (Savant, Farmingdale, N.Y.) resuspended in 10 µl H₂O, and reduced to 3.0 µl in a SPEEDVAC. Fluorescent nucleotide analogs were purchase from DuPont NEN (Boston, Mass.).

D. Hybridization of Reporter-labeled Nucleic Acid to Target DNA

Hybridization reactions contained 1.0 µl of fluorescent cDNA synthesis product (~2 µg) and 1.0 µl of hybridization buffer (10× SSC, 0.2% sodium dodecyl sulfate; SDS). The 2.0 µl probe mixtures were aliquoted onto the microarray surface and covered with 12 mm round cover slips. Arrays were transferred to a waterproof slide chamber having a cavity just slightly larger than a microscope slide. The chamber was kept at 100% humidity internally by the addition of 2 microliters of water in a corner of the chamber. The chamber containing the arrays was incubated for 18 hr at 65° C.

The arrays were washed for 5 minutes at room temperature (25° C.) in low stringency wash buffer (1× SSC, 0.1% SDS), then for 10 minutes at room temperature in high stringency wash buffer (0.1× SSC, 0.1% SDS). Arrays were scanned in 0.1× SSC using a fluorescence laser scanning device (see below).

E. Detection of Hybridized Sequences

The microscope used to detect the reporter-labeled hybridization complexes was outfitted with an Innova 70 mixed gas 10 W laser (Coherent Lasers, Santa Clara, Calif.) capable of generating a number of spectral lines, including lines at 488 nm and 568 nm. The excitation laser light was focused on the array using a 20× microscope objective (Nikon).

The slide containing the array was placed on a computer-controlled X-Y stage on the microscope and raster-scanned past the objective. The 1.8 cm×1.8 cm array used in the present example was scanned with a resolution of 20 µm. Spatial resolutions up to a few micrometers are possible with appropriate optics.

In two separate scans, a mixed gas multiline laser excited the two fluorophores sequentially. Emitted light was split, based on wavelength, into two photomultiplier tube detectors (PMT R1477, Hamamatsu Photonics, San Jose, Calif.) corresponding to the two fluorophores. Appropriate filters positioned between the array and the photomultiplier tubes were used to filter the signals. The emission maxima of the fluorophores used were 517 nm (fluorescein) and 588 nm (lissamine). Each array was typically scanned twice—one scan per fluorophore, using the appropriate filters at the laser source—although the apparatus was capable of recording the spectra from both fluorophores simultaneously.

The sensitivity of the scans was typically calibrated using the signal intensity generated by an MRNA or cDNA control species added to the hybridization mix at a known concentration. For example, in the experiments described in Example 2, human acetylcholine receptor mRNA was added to the wild-type Arabidopisis poly-A total mRNA sample at a weight ratio of 1:10,000. A specific location on the array contained a complementary DNA sequence, allowing the intensity of the signal at that location to be correlated with a weight ratio of hybridizing species of 1:10,000.

When messenger nucleic acids-derived probes containing two different fluorophores (e.g., representing test and control cells) are hybridized to a single array for the purpose of identifying genes that are differentially expressed, a similar calibration scheme may be employed to normalize the sensitivity of the photomultiplier tubes such that genes expressed at the same levels in the test and control samples display the same pseudocolor intensity. In one embodiment, this calibration is done by labeling samples of the calibrating cDNA with the two fluorophores and adding identical amounts of each to the hybridization mixture.

It will be understood that where greater confidence in the absolute levels of expression is desired, multi-point calibrations may be performed.

F. Analysis of Patterns of Reporter Levels The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). Exemplary images generated using this method are shown in FIGS. 7A, 7B, 8A, 8B, 9A and 9B.

The data were also analyzed quantitatively. In cases where two different fluorophores were used simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for the above analyses was similar in functionality to "IMAGE-QUANT", available from Molecular Dynamics (Sunnyvale, Calif.).

EXAMPLE 2

Two-color Detection of Differential Gene Expression in Wild Type versus Transgenic *Arabidopisis* Tissue.

Differential gene expression was investigated using a simultaneous, two-color hybridization scheme, which served to minimize experimental variation inherent in comparing independent hybridizations. Two µg of wild-type *Arabidopisis* total cDNA that were labeled with fluorescein (as above) were combined with two micrograms of transgenic *Arabidopisis* total cDNA that were labeled by incorporating lissamine-5-dCTP (DuPont NEN) in the reverse transcription step and hybridized simultaneously to a microarray containing the same pattern of spotted cDNAs as described in Example 1.

To test whether overexpression of a single gene could be detected in a pool of total *Arabidopisis* mRNA, methods of the invention were used to analyze a transgenic line overexpressing the transcription factor HAT4 (Schena, et al.). The transgenic *Arabidopisis* tissue was known to express HAT4 at levels of 0.5% of the total transcripts, while wild-type expression of HAT4 was only 0.01% of total transcripts (as previously determined by Northern analysis; Schena, et al.).

Human acetylcholine receptor mRNA was added to the wild-type *Arabidopisis* poly-A total mRNA sample at a weight ratio of 1:10,000 and into the transgenic *Arabidopisis* poly-A total mRNA sample at a weight ratio of 1:100 to roughly match the expected expression levels of HAT4.

As a cross-check of the negative controls, linear PCR (e.g., Cole, et al., Manoni, et al.) was used to generate single-stranded fluorescein-labeled rat glucocorticoid receptor DNA and lissamine-labeled yeast TRP4 DNA. The two PCR products were added to the hybridization solution at a partial concentration of ~1:100. The two fluorophores were excited separately in two separate scans in order to minimize optical crosstalk.

The array was then scanned separately for fluorescein and lissamine emission following independent excitation of the two fluorophores as described in Example 1, above. The results of the experiments are shown in FIGS. 8A and 8B, discussed above.

EXAMPLE 3

Two-color Detection of Differential Gene Expression in Root versus Leaf Tissue.

In a similar experiment using the same labeling and hybridization procedures described above, 2 μg of total cDNA from *Arabidopisis* root tissue labeled with fluorescein were combined with two micrograms of total cDNA from *Arabidopisis* leaf tissue labeled with lissamine and were simultaneously hybridized to a microarray containing the same pattern of target sequences described above. The acetylcholine gene mRNA was added to both poly-A total mRNA samples at 1:1,000 to allow for normalization of fluorescence intensities. The glucocorticoid and TRP4 controls were added to the hybridization probe as before. The results are shown in FIGS. 9A and 9B, discussed above.

Although the invention has been described with respect to specific embodiments and methods, it will be clear that various changes and modification may be made without departing from the invention.

It is claimed:

1. A subarray comprising discrete regions containing only distinct gene sequences which are characterized by an average of at least 2 fold elevation or reduction in expression levels in test cells, when compared with expression levels of the same genes in control cells, wherein the subarray comprises distinct gene sequences with each distinct gene sequence having at least 50 subunits in length and disposed at a separate, defined position in said subarray.

2. The subarray of claim 1, wherein said distinct gene sequences are obtained from multiple tissue sources.

3. The subarray of claim 1, wherein the distinct gene sequences are expressed sequence tag (EST) genes.

4. The subarray of claim 1, comprising gene sequences whose expression levels in peripheral blood cells are affected by a selected condition, wherein the test cells are peripheral blood cells so affected, and the control cells are peripheral blood cells from normal individuals.

5. The subarray of claim 1, comprising gene sequences whose expression levels are specifically related to a tumor state, wherein the test cells are neoplastic cells from a selected tissue, and the control cells are normal cells from the same tissue type.

6. The subarray of claim 1, comprising gene sequences whose expression levels are specifically related to a genetic disease, wherein the test cells are cells from a tissue whose functioning is affected by the disease, and the control cells are cells from the same tissue in a normal individual.

7. The subarray of claim 1, comprising gene sequences whose expression levels are specifically related to a virus-infected cell, wherein the test cells are virus-infected cells, and the control cells are uninfected cells of the same cell type from a non-infected individual.

8. The subarray of claim 1, comprising gene sequences whose expression levels are specifically related to immune cells under immunological challenge, wherein the test cells are immunologically challenged immune cells, and the control cells are non-challenged immune cells of the same cell type.

9. The sub array of claim 1, comprising gene sequences whose expression levels are specifically related to drug response in a given test cell type, wherein the test cells are cells exposed to the drug, and the control cells are cells of the same type not exposed to the drug.

10. The subarray of claim 1, consisting of discrete regions of distinct gene sequences that are at least 50 subunits in length.

* * * * *

UNITED STATES PATENT AND TRADEMARK OFFICE
CERTIFICATE OF CORRECTION

| | |
|---|---|
| PATENT NO. | : 7,625,697 B2 |
| APPLICATION NO. | : 09/908304 |
| DATED | : December 1, 2009 |
| INVENTOR(S) | : Tidhar Dari Shalon et al. |

Page 1 of 1

It is certified that error appears in the above-identified patent and that said Letters Patent is hereby corrected as shown below:

Column 1, lines 13-15, delete "The United States government may have certain rights in the present invention pursuant to Grant No. HG00450 by the National Institutes of Health." and insert --This invention was made with Government support under contract HL002668 awarded by the National Institutes of Health. The Government has certain rights in this invention.--

Signed and Sealed this

Twenty-fifth Day of May, 2010

David J. Kappos
*Director of the United States Patent and Trademark Office*